United States Patent [19]

Wages

[11] 4,216,027
[45] Aug. 5, 1980

[54] METHOD AND APPARATUS FOR CLEANSING AND DISINFECTING A FLUSHING TOILET

[75] Inventor: Dwight E. Wages, Terrace Park, Ohio

[73] Assignee: The Procter & Gamble Company, Cincinnati, Ohio

[21] Appl. No.: 897,479

[22] Filed: Apr. 18, 1978

[51] Int. Cl.$^2$ .................... B08B 3/08; E03D 9/03
[52] U.S. Cl. ........................................ 134/36; 4/228
[58] Field of Search .............. 134/36, 28, 29, 95, 134/100; 422/28, 33, 37, 263, 266; 4/224, 227, 228

[56] References Cited

U.S. PATENT DOCUMENTS

| | | | |
|---|---|---|---|
| 1,307,535 | 6/1919 | Ciancagini | 4/224 |
| 2,497,057 | 2/1950 | Pape et al. | 252/142 |
| 3,121,236 | 2/1964 | Yadro et al. | 4/228 |
| 3,289,887 | 12/1966 | Farrar et al. | 222/1 |
| 3,339,801 | 9/1967 | Hronas | 4/228 X |
| 3,423,182 | 1/1969 | Klasky | 422/266 |
| 3,504,384 | 4/1970 | Radley et al. | 4/228 |
| 3,604,020 | 9/1971 | Moisa | 4/228 |
| 3,769,640 | 11/1973 | Castronouo | 4/228 |
| 3,867,101 | 2/1975 | Herring | 4/228 X |
| 3,952,339 | 4/1976 | Baur et al. | 4/228 |

*Primary Examiner*—Richard V. Fisher
*Attorney, Agent, or Firm*—E. Kelly Linman; John V. Gorman; Richard C. Witte

[57] ABSTRACT

Method and apparatus for cleansing and disinfecting a flushing toilet comprising a toilet tank and a toilet bowl by treating the water discharged from the toilet tank each time the toilet is flushed. First and second passive dispensing apparatus for immersion in the toilet tank water are provided to carry out the cleansing and disinfecting method. The first passive dispensing apparatus contains a solid, water soluble, surfactant containing cake for exposure to a quantity of water to form an aqueous surfactant containing solution within the first dispensing apparatus. The second passive dispensing apparatus contains a solid, water soluble, disinfectant containing cake for exposure to a second quantity of water to form an aqueous, disinfectant containing solution within the second dispensing apparatus. Each dispensing apparatus isolates both the cake and the aqueous solution made therefrom from the water surrounding the dispensing apparatus intermediate flush cycles of the toilet and discharges a predetermined quantity of aqueous solution into the toilet tank when the toilet is flushed. The first dispensing apparatus is so constructed that the aqueous surfactant containing solution discharged therefrom is of substantially constant strength, while the second dispensing apparatus is so constructed that the aqueous disinfectant containing solution discharged therefrom is substantially free of undissolved solids. The isolation provided by each dispensing apparatus permits co-dispensing surfactant containing and disinfectant containing aqueous solutions which chemically react with one another upon contact to provide effective cleansing and disinfecting of the toilet.

12 Claims, 44 Drawing Figures

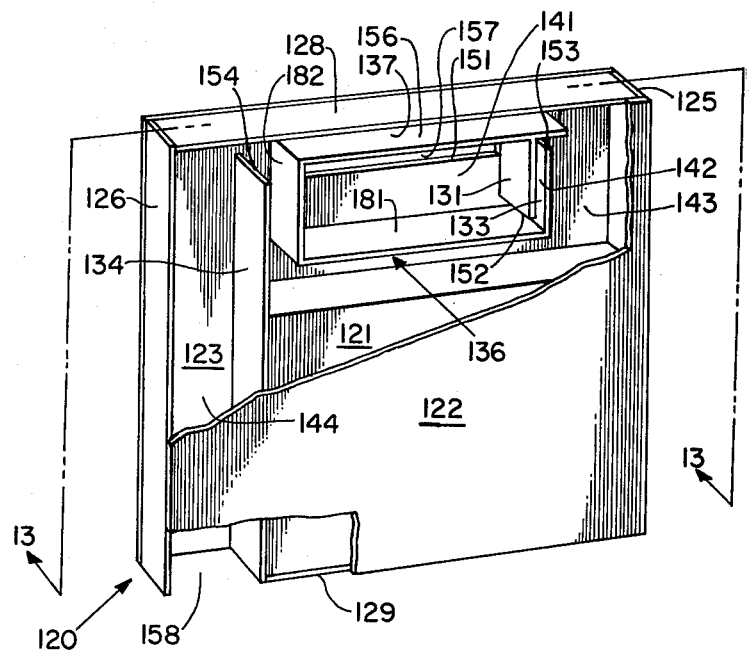
Fig. 12
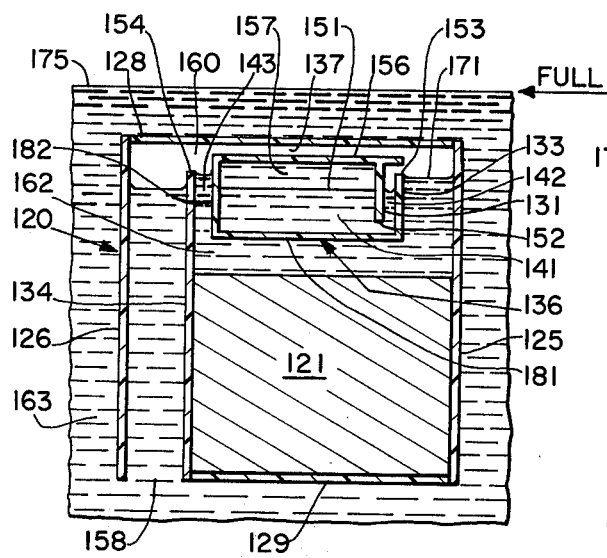
Fig. 13
Fig. 14

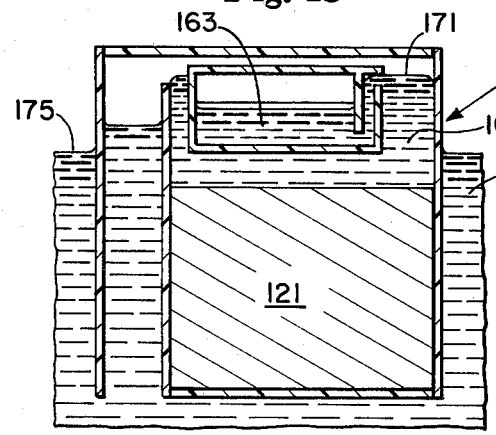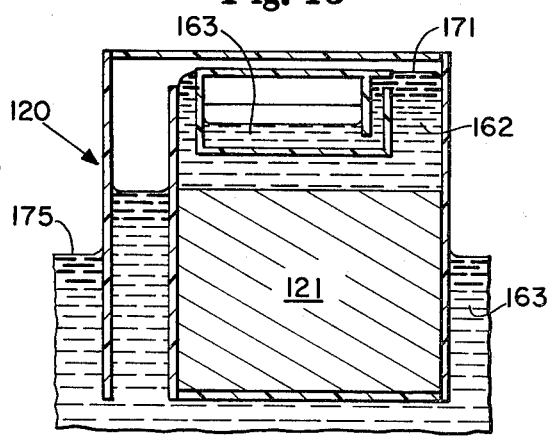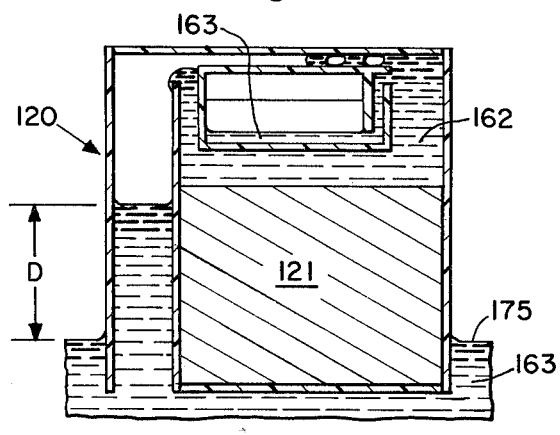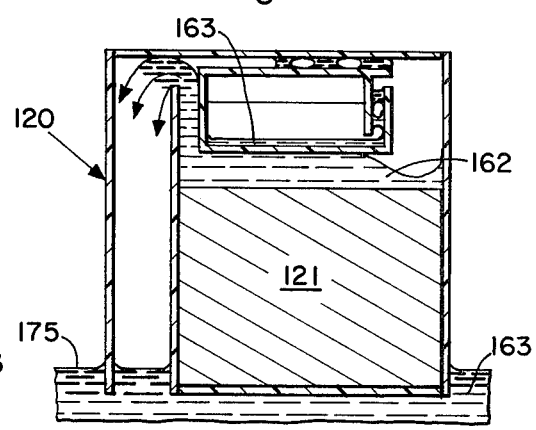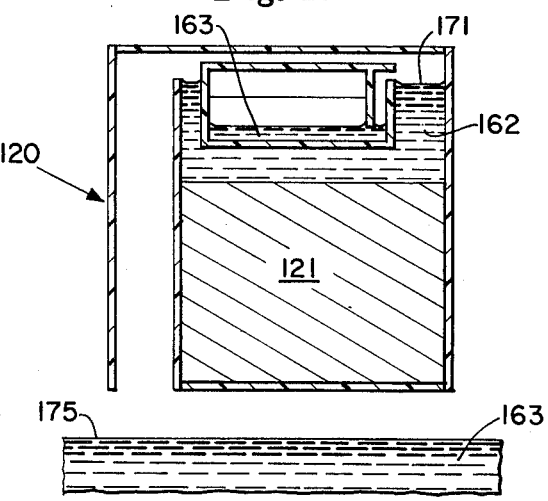

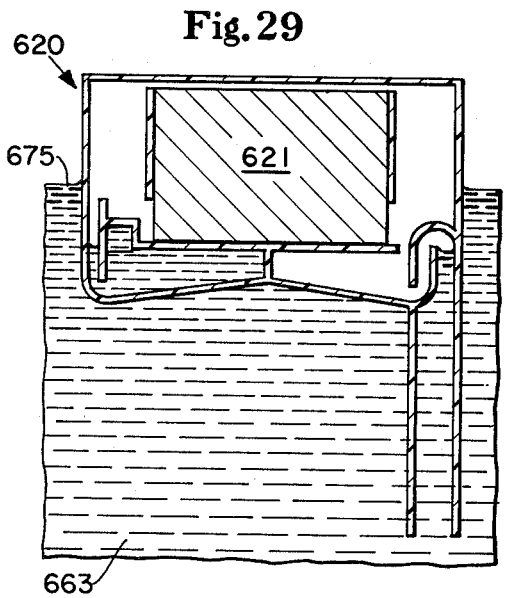
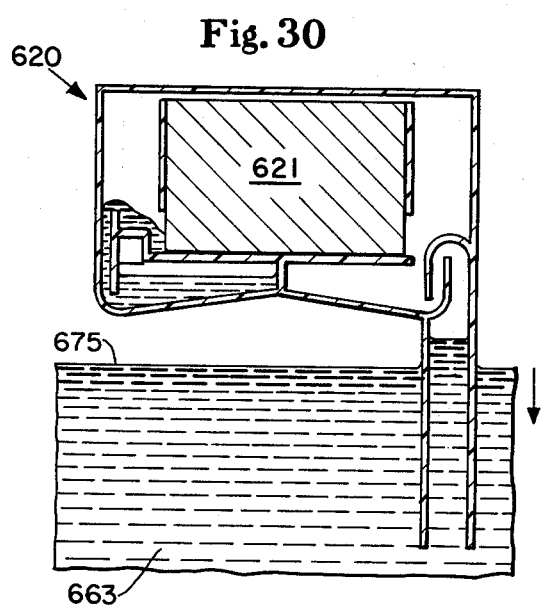
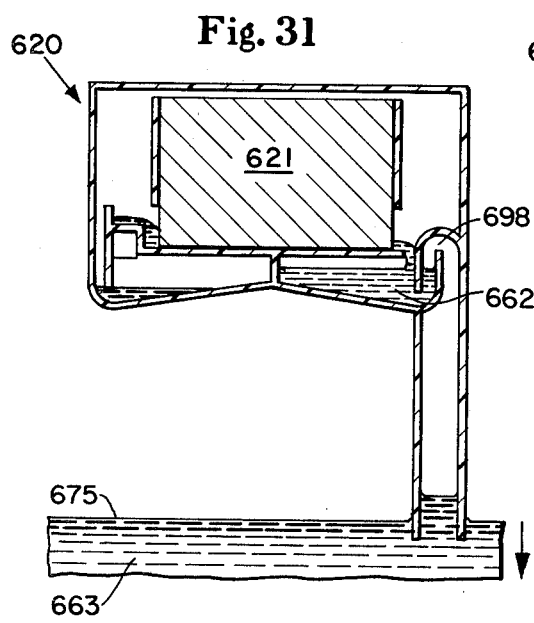
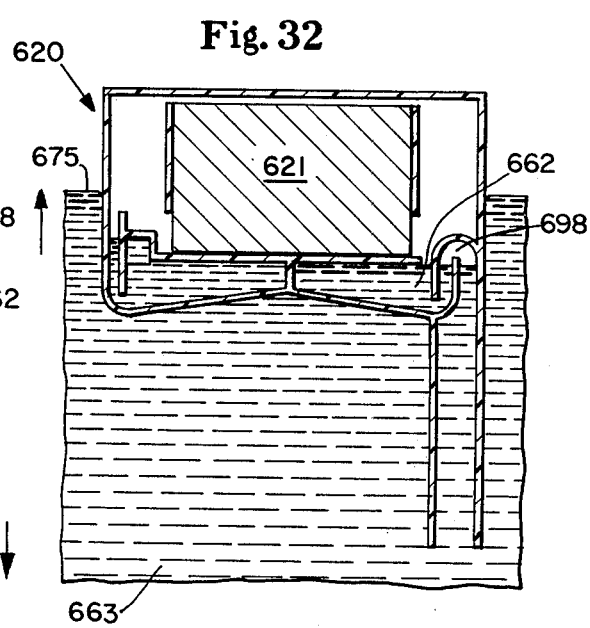

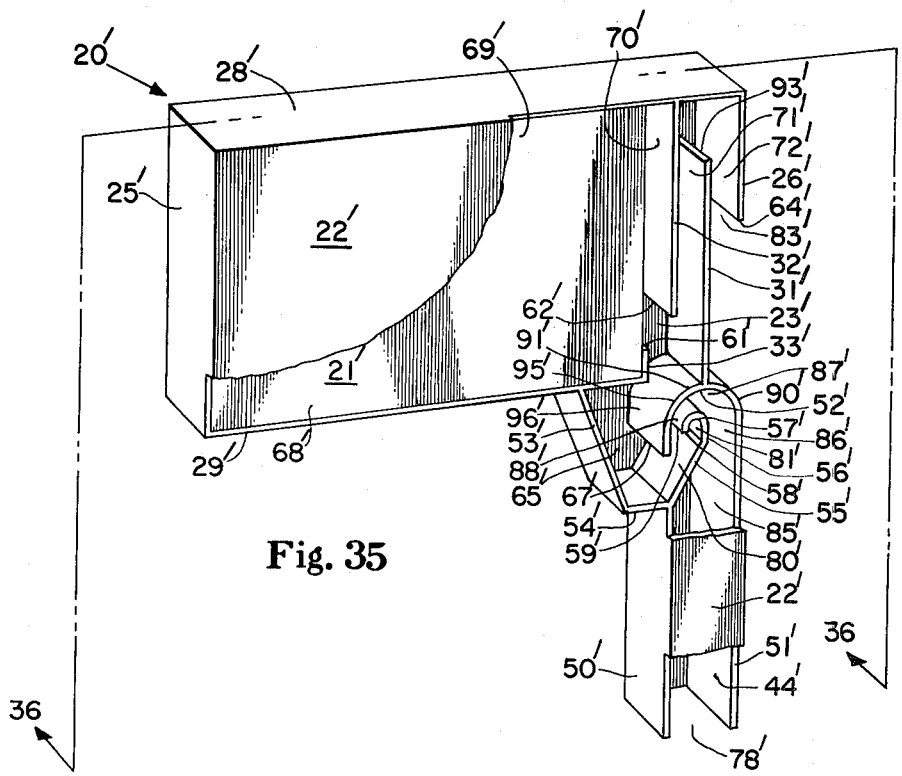
Fig. 35
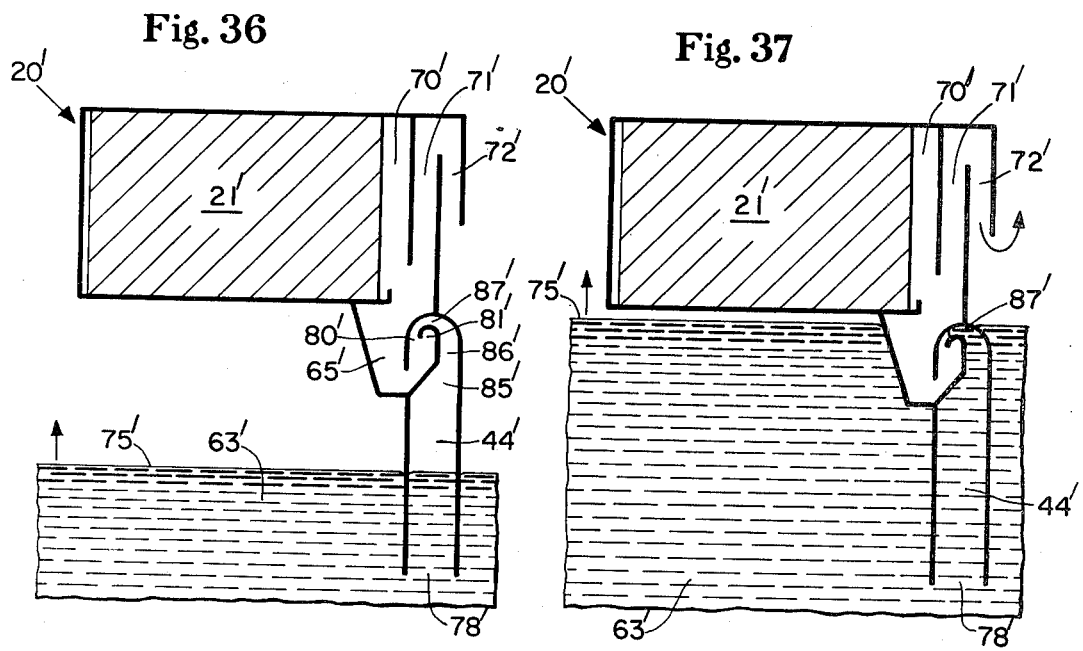
Fig. 36
Fig. 37

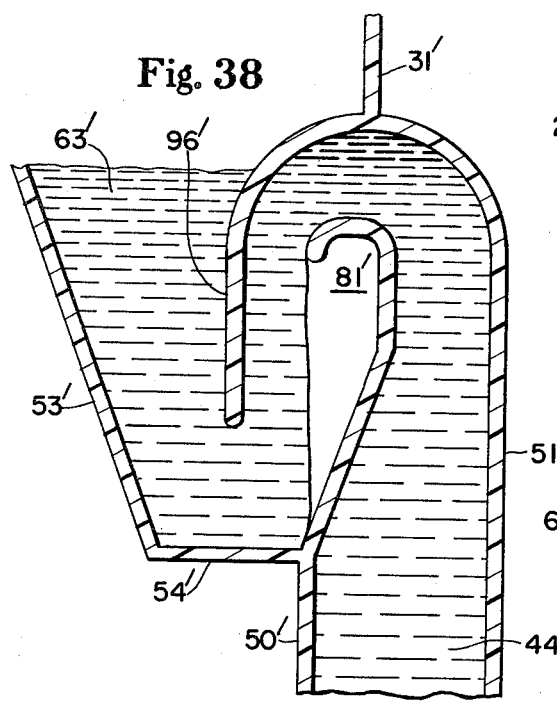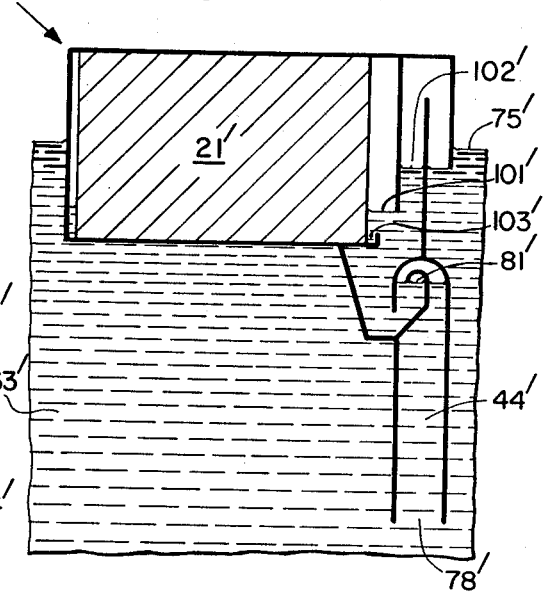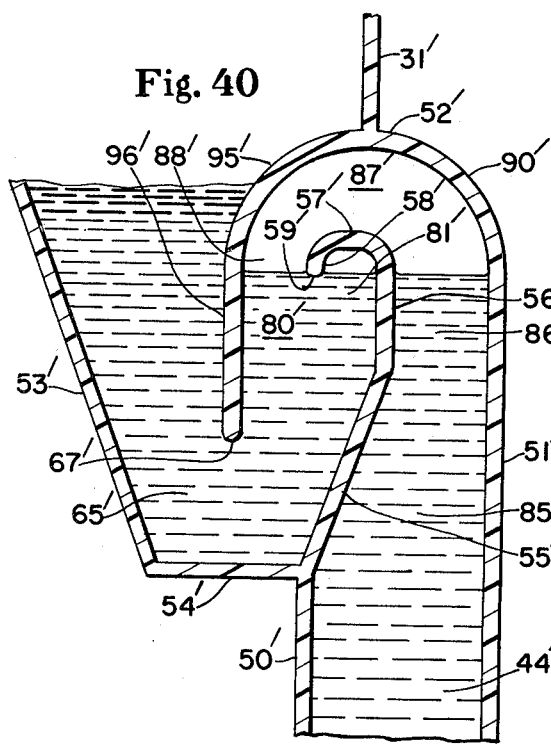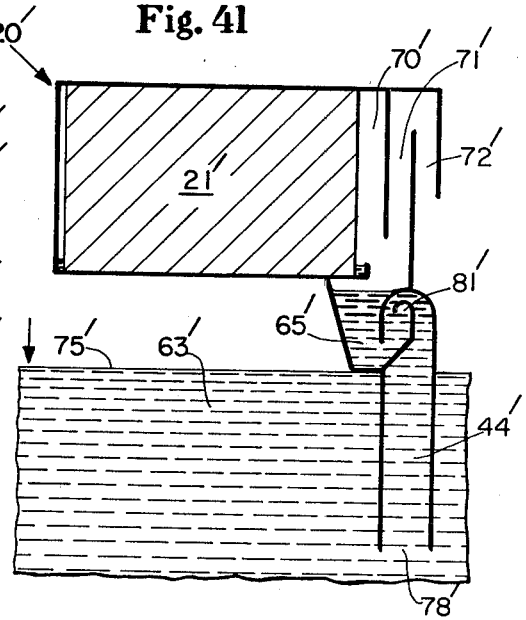

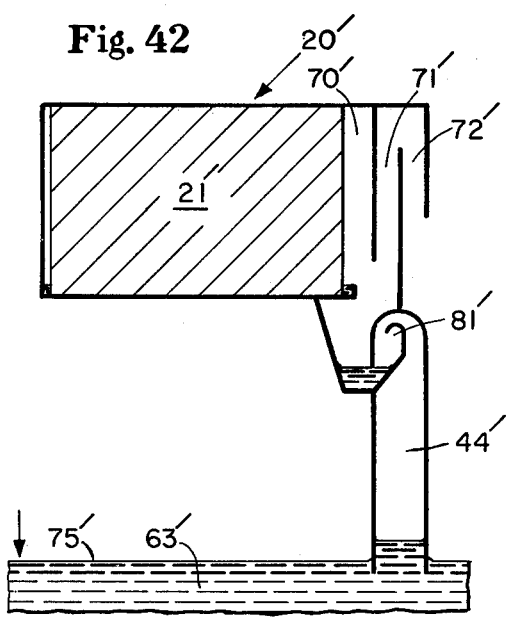
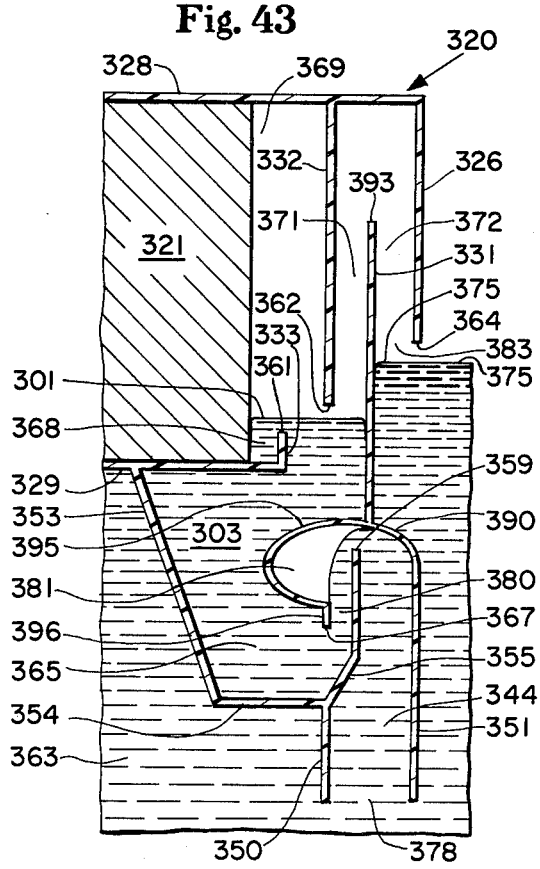
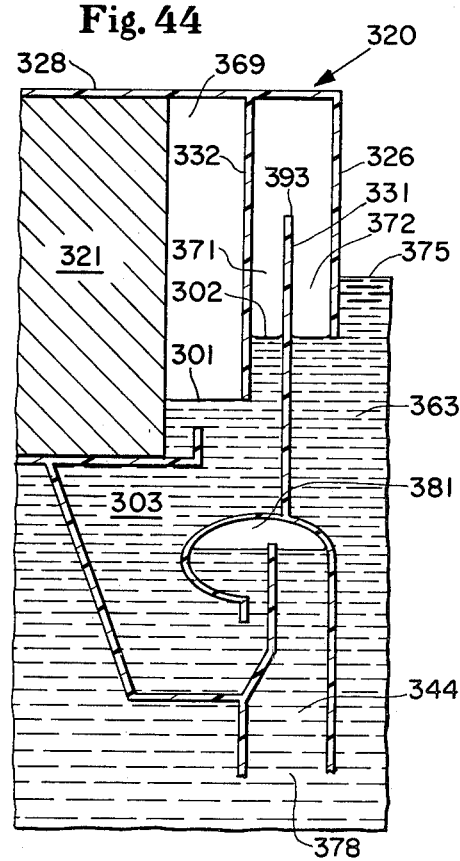

METHOD AND APPARATUS FOR CLEANSING AND DISINFECTING A FLUSHING TOILET

FIELD OF THE INVENTION

The present invention pertains, in general, to method and apparatus for cleansing and disinfecting a flushing toilet comprising a toilet tank and a toilet bowl each time the toilet is flushed. Because the preferred dispensing apparatus employed is entirely passive, i.e., it has no moving parts, the present invention relates to apparatus for carrying out said method which is both economical to manufacture and highly reliable in operation. Furthermore, because a predetermined quantity of solution is discharged each time the toilet is flushed, the present invention relates to plural product dispensers which are so sized with respect to one another that each of the product components will be consumed at about the same point in time, thereby minimizing waste of any particular component. In addition, the present invention has particular relation to cleansing and disinfecting apparatus which maintains each product component and the solution formed therefrom in isolation from the toilet tank water and from the other components disposed in other independent sections of the dispensing apparatus, thus making it possible to co-dispense aqueous solutions which would adversely react with one another if allowed to combine in sufficiently high concentration prior to flushing of the toilet.

BACKGROUND OF THE INVENTION

Various devices for cleansing and disinfecting flushing toilets are well known in the art. U.S. Pat. No. 1,307,535 issued to Ciancoglini on June 24, 1919 discloses dispensing a disinfectant into a flush tank type toilet at the end of the flush cycle. U.S. Pat. No. 3,339,801 issued to Hronas on Sept. 5, 1967 discloses the introduction of various agents including detergents, biocides, corrosion inhibitors, scale inhibitors, deodorants, etc. into the flush tank as it fills, thus treating the entire water content of the tank. U.S. Pat. No. 3,121,236 issued to Yadro et al on Feb. 18, 1964 discloses dispensing into the toilet tank compositions containing such materials as silicates, phosphates, and carbonates to treat metal ions in the water and thereby provide rust and scale prevention. U.S. Pat. No. 3,504,384 issued to Radley et al on Apr. 7, 1970 discloses apparatus for separately dispensing a detergent composition and a disinfecting composition into the flush tank of a toilet. It is indicated that dual dispensing is desirable since the disinfectant and detergent materials are often incompatible with each other. The apparatus is designed to hang below the high water line of the toilet tank. In a preferred embodiment of the Radley et al device, the detergent composition in the form of a cake resides in an enclosed compartment, and as the flush tank fills, water enters and fills the compartment, whereupon a concentrated solution of detergent forms in said compartment. The compartment is not, however, isolated from the surrounding toilet tank water. A separate compartment contains a disinfectant composition in cake form which is in constant contact with the water in the tank and gradually dissolves in the tank to form a dilute disinfectant solution. Upon flushing, the detergent solution from the first compartment flows out of the compartment when the level of flush water in the tank falls below the level of the compartment.

Thus, it is clear that the desirability of separating organic materials, i.e., surfactants, perfumes, dyes, etc., from disinfecting agents, particularly those that are strong oxidizing agents is recognized in the prior art. If these materials are not isolated from each other prior to use, the organic material is susceptible to chemical interaction with the oxidizing agent, thereby resulting in a loss of available chlorine or oxygen, and a corresponding loss of disinfecting, deodorizing and cleaning performance. The prior art fails, however, to teach or disclose suitable passive dispensing apparatus capable of completely isolating the chemicals from the toilet tank water, and hence from one another during quiescent periods intermediate flushes of the toilet.

It is further known in the prior art that disinfectant tablets or cakes, when submerged in water, release active ingredients to form an aqueous solution of the disinfectant and, in addition, may release soluble inorganic filler/stabilizing salts. Such solublization results in the formation of a concentration gradient which is highest at the bottom of the solution and lowest at the top surface of the solution. Furthermore, insoluble salts which may be formed by ion exchange with the disinfectant tablet materials and undissolved disinfectant particles which tend to break off from the tablet as it dissolves tend to settle to the bottom of the solution. Prior art passive dispensing apparatus, i.e., dispensing apparatus having no moving parts, have not solved the problem of reliably dispensing a predetermined quantity of such disinfectant solutions with each flush cycle of the toilet without simultaneously discharging these undissolved solid materials which are undesirable in the toilet tank and bowl, since they may cause corrosion of metal components within the toilet tank and result in a waste of disinfectant materials.

Another problem known in the prior art when attempting to employ a surfactant containing cleansing cake in a prior art style toilet tank dispenser is that the surfactant containing cake forms a thick, densified solution when exposed to water, which densified solution tends to settle to the bottom of the solution reservoir, thereby forming viscosity and concentration gradients between the bottom and the top surfaces of the solution. Prior art style passive dispensing apparatus have not solved the problem of reliably discharging a predetermined quantity of such a surfactant containing solution of substantially constant strength each time the toilet is flushed.

In summary, none of the discovered prior art has solved all of the aforementioned problems associated with co-dispensing a predetermined quantity of surfactant containing cleansing solution with a predetermined quantity of disinfectant containing solution in the manner of or to the degree provided by the present invention utilizing passive dispensing apparatus having no moving parts and providing complete isolation of each product component from the toilet tank water during quiescent periods intermediate flush cycles.

SUMMARY OF THE INVENTION

In accordance with a preferred embodiment of the present invention, a method for cleansing and disinfecting a flushing toilet comprising a toilet tank and a toilet bowl each time said toilet is flushed is provided. Briefly, said method comprises: (a) forming a quantity of surfactant containing solution by exposing a first solid, water soluble, surfactant containing cake to a first quantity of water within a first passive dispensing apparatus immersed in a toilet tank; (b) isolating said first cake and said surfactant containing solution in said first passive dispensing apparatus from the surrounding water; (c) forming a quantity of disinfectant containing solution by totally immersing a second solid, water soluble, disinfectant containing cake in a second quantity of water within a second passive dispensing apparatus immersed in the toilet tank; (d) isolating said second cake and said disinfectant containing solution in said second passive dispensing apparatus from the surrounding water; (e) flushing the toilet, thereby lowering the water level in said toilet tank from a first elevation to a second elevation; (f) discharging a predetermined quantity of said surfactant containing solution of substantially constant strength from said first passive dispensing apparatus in response to the water level in said toilet tank being lowered from said first elevation to said second elevation; and (g) discharging a predetermined quantity of said disinfectant containing solution substantially free of undissolved solids from said second passive dispensing apparatus in response to the water level in said toilet tank being lowered from said first elevation to said second elevation.

Preferred apparatus for carrying out the aforementioned cleansing and disinfecting method are also provided.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 12 is a partially torn away perspective view of another embodiment of a passive dosing dispenser suitable for dispensing a disinfectant containing solution in accordance with the present invention;

FIGS. 13-19 are simplified sequential sectional views which show a portion of a cycle of the dispenser shown in FIG. 12 and which views are taken along section line 13—13 of FIG. 12;

FIGS. 27-34 are simplified sequential sectional views which show a portion of a cycle of the dispenser shown in FIG. 26 and which views are taken along section line 27—27 of FIG. 26;

FIG. 35 is a partially torn away perspective view of another passive dosing dispenser suitable for dispensing a surfactant containing solution in accordance with the present invention;

FIGS. 36, 37, 39, 41 and 42 are simplified, sequential sectional views which show a portion of a cycle of the dispenser shown in FIG. 35 and which views are taken along section line 36—36 of FIG. 35;

FIG. 38 is an enlarged fragmentary sectional view of the air trap portion of the dispenser of FIG. 35;

FIG. 40 is an enlarged fragmentary sectional view of the air trap portion of the dispenser of FIG. 35 in the condition illustrated in FIG. 39;

FIG. 43 is a fragmentary sectional view of yet another embodiment of a passive dosing dispenser suitable for dispensing a surfactant containing solution in accordance with the present invention shown as the water level is rising in the toilet tank; and FIG. 44 is a fragmentary sectional view of the dispenser of FIG. 43 shown after the water has reached its FULL level in the toilet tank.

DESCRIPTION OF THE PREFERRED EMBODIMENTS

Figure 1:
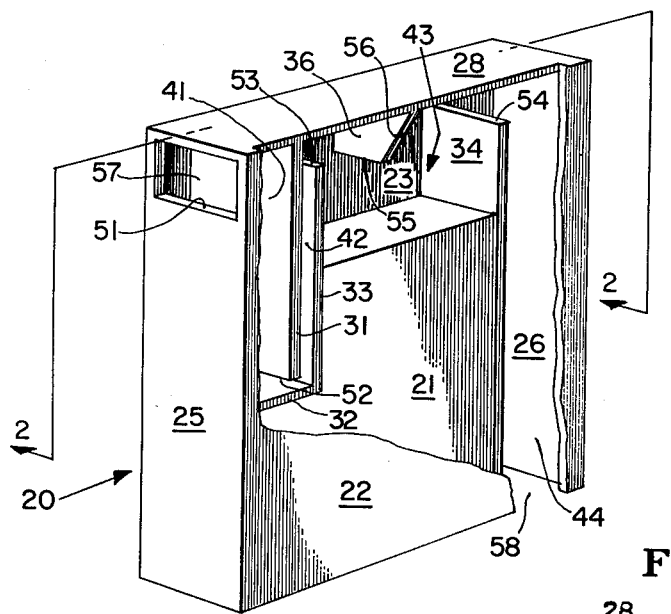
FIG. 1 is a partially torn away perspective view of a passive dosing dispenser suitable for dispensing a disinfectant containing solution in accordance with the present invention.

It is known in the art that disinfectant type cleaners are useful in providing cleaning, deodorizing, and disinfecting benefits when used for toilet bowl maintenance. The prior art makes numerous references to specific formulations to achieve these benefits. For example, U.S. Pat. No. 3,604,020 issued to Moisa on Sept. 14, 1971 suggests the use of calcium hypochlorite as a disinfectant agent, U.S. Pat. No. 2,497,057 issued to Pape et al on Feb. 7, 1950 suggests the use of compressed acid sulfate tablets, and U.S. Pat. No. 3,504,384 issued to Radley et al on Apr. 7, 1970 discloses the use of trichloroisocyanuric acid as a disinfectant, said patents being hereby incorporated herein by reference.

Any suitable disinfectant agent which yields active chlorine or active oxygen in aqueous solution can be employed to advantage in the practice of the present invention. This is typically the case for materials used as bleaching agents. Thus, bleaches represent a particularly preferred form of disinfecting agent suitable for use in the practice of the present invention.

A highly preferred bleaching disinfecting agent is one which yields a hypochlorite species in aqueous solution. The hypochlorite ion is chemically represented by the formula $OCl^-$. The hypochlorite ion is a strong oxidizing agent and for this reason materials which yield this species are considered to be powerful disinfecting agents.

At lower pH levels, aqueous solutions formed by dissolving hypochlorite-yielding compounds contain active chlorine partially in the form of hypochlorous acid moieties and partially in the form of hypochlorite ions. At pH levels above about 10, essentially all of the active chlorine is in the form of hypochlorite ion.

Those disinfecting agents which yield a hypochlorite species in aqueous solution include alkali metal and alkaline earth metal hypochlorites, hypochlorite addition products, chloramines, chlorimines, chloramides, and chlorimides. Specific examples of compounds of this type include lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, trichlorocyanuric acid, sodium dichloroisocyanurate, sodium dichloroisocyanurate dihydrate, 1,3-dichloro-5,5-dimethylhydantoin, N-chlorosulfamide, Chloramine T, Dichlormaine T, Chloramine B and Dichloramine B. A particularly preferred disinfecting formula suitable for use in the practice of the present invention is described in the commonly assigned U.S. Patent Application of John Daniel Nyquist entitled DISINFECTING COMPOSITION, Ser. No. 897,478, filed concurrently herewith and now abandoned, said patent application being hereby incorporated herein by reference.

Examples of disinfecting agents which yield active oxygen in aqueous solution are sodium perborate and potassium monopersulfate ($KHSO_5$).

Although there are circumstances where the use of such disinfecting agents in a loose granule form may be advantageous, generally it is preferable to compress the disinfectant agents into a tablet or cake with the use of equipment such as tableting presses, extruders, chilsonaters, etc. Such compaction helps to regulate the solubility of the disinfecting agents while allowing for a more efficient use of space in relation to size and fit of suitable dispensing apparatus into the toilet tank of a flushing toilet.

Disinfecting agents of the type described above may comprise from about 10% to about 100% of the disinfecting formula by weight when utilized in conjunction with the practice of the present invention.

For disinfectant compositions suited for use in the practice of the present invention, disinfectant agent stabilization is generally achieved by careful selection of disinfecting agents and noninterfering inorganic filler salts.

For solid systems containing bleach, it is generally desirable to include a stabilizer for the bleaching agents. For some types of bleaching agents, particularly oxygen bleaching agents, this material can be a water-soluble bleach stabilizing agent selected from the group consisting of alkali metal, alkaline earth metal, ammonium and substituted ammonium salts of an acid having an ionization constant at 25° C., for the first hydrogen, of at least about $1 \times 10^{-3}$. Stabilizing salts include the alkali metals, alkaline earth metals, ammonium, and substituted ammonium sulfates, bisulfates, nitrates, silicates, chlorides, phosphates, pyrophosphates, polyphosphates and hexametaphosphates. Specific examples of such materials include magnesium sulfate, sodium sulfate, potassium sulfate, ammonium sulfate, lithium sulfate, dimethylammonium sulfate, sodium chloride, lithium chloride, potassium chloride, sodium bisulfate, potassium bisulfate, ammonium bisulfate, sodium nitrate, magnesium nitrate, calcium nitrate, sodium tripolyphosphate, trisodium phosphate, sodium metaphosphate, sodium hexametaphosphate, potassium pyrophosphate, sodium tetraphosphate, sodium silicate, and sodium metasilicate. Stabilizing agents of this type are described more fully in U.S. Pat. No. 3,639,285 issued to Nielsen on Feb. 1, 1972, said patent being hereby incorporated herein by reference.

For chlorine bleaching agents, particularly Nchloroimides, a highly preferred stabilizing agent is sodium acetate. Use of this material as a bleach stabilizer is described more fully in U.S. Pat. No. 3,829,385 issued to Abbott et al on Aug. 13, 1974, said patent being hereby incorporated herein by reference.

In solid compositions suitable for use in the practice of the present invention such disinfectant stabilizing agents are preferably utilized to the extent of from about 1% to about 90% by weight of the composition.

It is also known in the prior art that detergent or surfactant compositions are useful in providing cleansing and deodorizing benefits to a toilet bowl. As utilized herein, the terms detergent and surfactant are utilized interchangeably to refer to those surfactants which are normally utilized as detergent ingredients. U.S. Pat. No. 3,769,640 issued to Castronovo on Nov. 6, 1973, U.S. Pat. No. 3,867,101 issued to Herring on Feb. 18, 1975 and U.S. Pat. No. 3,504,384 issued to Radley et al on Apr. 7, 1970, which patents are hereby incorporated herein by reference, are representative of the prior art.

Surfactant compositions useful in the practice of the present invention preferably contain from about 20% to about 95% by weight of a surfactant or combination of surfactants selected from the group consisting of anionic, nonionic, ampholytic, and zwitterionic surface active agents. In addition, these compositions can include dye (0–15% by weight) as an indicator of dispenser functionality, perfume ingredients (0–25% by weight) to provide odor benefits, and salts (0–30% by weight) as processing aids. The aforesaid surfactant compositions are preferably used in connection with the practice of the present invention in the form of compressed cakes made via extrusion or hydraulic stamping, or as a solid made by pouring a melt of surfactant into a mold and allowing it to solidify upon cooling.

Anionic surfactants operable in compositions suitable for use in practicing the present invention can be broadly described as the water-soluble salts, particularly the alkali metal salts, of organic sulfuric acid reaction products having in their molecular structure an alkyl or alkyl aryl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic surfactants which can be employed in practicing the present invention are the sodium or potassium alkyl sulfates, especially those obtained by sulfating the higher alcohols ($C_8$–$C_{18}$ carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); paraffin sulfonate surfactants having the general formula $RSO_3M$, wherein R is a primary or secondary alkyl group containing from about 8 to about 22 carbon atoms (preferably 10 to 18 carbon atoms) and M is an alkali metal, e.g., sodium or potassium; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 10 moles of ethylene oxide; sodium or potassium salts of alkyl phenol ethylene oxide ether sulfates with about 1 to about 10 units of ethylene oxide per molecule and in which the alkyl radicals contain from 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium β-acetoxy- or β-acetamido-alkanesulfonates where the alkane has from 8 to 22 carbon atoms.

Nonionic surface active agents operable in compositions suitable for use in practicing the present invention can be of three basic types—the alkylene oxide condensates, the amides and the semi-polar nonionics.

The alkylene oxide condensates are broadly defined as compounds produced by the condensation of alkylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble-compound having the desired degree of balance between hydrophilic and hydrophobic elements.

Examples of such alkylene oxide condensates include:

1. The condensation products of aliphatic alcohols with ethylene oxide. The alkyl chain of the aliphatic alcohol can either be straight or branched and generally contains from about 8 to about 22 carbon atoms. Examples of such ethoxylated alcohols include the condensation product of about 6 moles of ethylene oxide with 1 mole of tridecanol, myristyl alcohol condensed with about 10 moles of ethylene oxide per mole of myristyl alcohol, the condensation product of ethylene oxide with coconut fatty alcohol wherein the coconut alcohol is a mixture of fatty alcohols with alkyl chains varying from 10 to 14 carbon atoms and wherein the condensate contains about 6 moles of ethylene oxide per mole of alcohol, and the condensation product of about 9 moles of ethylene oxide with the above-described coconut alcohol. Examples of commercially available nonionic surfactants of this type include Tergitol 15-S-9 marketed by the Union Carbide Corporation, Neodol 23-6.5 marketed by the Shell Chemical Company and Kyro EOB marketed by The Procter & Gamble Company.

2. The polyethylene oxide condensates of alkyl phenols. These compounds include the condensation products of alkyl phenols having an alkyl group containing from about 6 to 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived, for example, from polymerized propylene, diisobutylene, octene, or nonene. Examples of compounds of this type include nonyl phenol condensed with about 9.5 moles of ethylene oxide per mole of nonyl phenol, dodecyl phenol condensed with about 12 moles of ethylene oxide per mole of phenol, dinonyl phenol condensed with about 15 moles of ethylene oxide per mole of phenol, di-isooctylphenol condensed with about 15 moles of ethylene oxide per mole of phenol. Commercially available nonionic surfactants of this type include Igepal CO-610 marketed by the GAF Corporation; and Triton X-45, X-114, X-100 and X-102, all marketed by the Rohm and Haas Company.

3. The condensation products of ethylene oxide with a hydrophobic base formed by the condensation of propylene oxide with propylene glycol. The hydrophobic portion of these compounds has a molecular weight of from about 1500 to 1800 and of course exhibits water insolubility. The addition of polyoxyethylene moieties to this hydrophobic portion tends to increase the water-solubility of the molecule. Examples of compounds of this type include certain of the commercially available Pluronic surfactants marketed by the Wyandotte Chemicals Corporation.

4. The condensation products of ethylene oxide with the product resulting from the reaction of propylene oxide and ethylene diamine. The hydrophobic base of these products consists of the reaction product of ethylene diamine and excess propylene oxide, said base having a molecular weight of from about 2500 to about 3000. This base is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds marketed by the Wyandotte Chemicals Corporation.

Examples of the amide type of nonionic surface active agent include the ammonia, monoethanol and diethanol amides of fatty acids having an acyl moiety of from about 8 to about 18 carbon atoms. These acyl moieties are normally derived from naturally occurring glycerides, e.g. coconut oil, palm oil, soybean oil and tallow, but can be derived synthetically, e.g., by the oxidation of petroleum, or by hydrogenation of carbon monoxide by the Fischer-Tropsch process.

Examples of the semi-polar type of nonionic surface active agents are the amine oxides, phosphine oxides and sulfoxides. These materials are described more fully in Berry, U.S. Pat. No. 3,819,528, issued June 25, 1974, and incorporated herein by reference.

Ampholytic surfactants operable in compositions suitable for use in practicing the present invention can be broadly described as derivatives of aliphatic amines which contain a long chain of about 8 to 18 carbon atoms and an anionic water-solubilizing group, e.g. carboxy, sulfo or sulfato. Examples of compounds falling within this definition are sodium 3-dodecylamino-propionate, sodium-3-dodecylamino propane sulfonate, and dodecyl dimelthylammonium hexanoate.

Zwitterionic surface active agents operable in compositions suitable for use in practicing the present invention are broadly described as internally-neutralized derivatives of aliphatic quaternary ammonium and phosphonium and tertiary sufonium compounds, in which the aliphatic radical can be straight chain or branched, and wherein one of the aliphatic substituents contains from about 8 to 18 carbon atoms and one contains an anionic water solubilizing group, e.g., carboxy, sulfo, sulfato, phosphato, or phosphono.

Bleach-stable surfactants which are especially resistant to oxidation are the alkyl sulfates and paraffin sulfonates. Alkyl sulfates are the water-soluble salts of sulfated fatty alcohols containing from about 8 to 18 carbon atoms in the alkyl group. Examples of suitable alcohols which can be employed in alkyl sulfate manufacture include decyl, lauryl, myristyl, palmityl and stearyl alcohols and the mixtures of fatty alcohols derived by reducing the glycerides of tallow and coconut oil.

Specific examples of alkyl sulfate salts which can be employed in the instant surfactant compositions include sodium lauryl alkyl sulfate, sodium stearyl alkyl sulfate sodium palmityl alkyl sulfate, sodium decyl sulfate, sodium myristyl alkyl sulfate, potassium lauryl alkyl sulfate, potassium stearyl alkyl sulfate, potassium decyl sulfate, potassium palmityl alkyl sulfate, potassium myristyl alkyl sulfate, sodium dodecyl sulfate, potassium dodecyl sulfate, potassium tallow alkyl sulfate, sodium tallow alkyl sulfate, sodium coconut alkyl sulfate, potassium coconut alkly sulfate and mixtures of these surfactants. Highly preferred alkyl sulfates are sodium coconut alkyl sulfate, potassium coconut alkyl sulfate, potassium lauryl alkyl sulfate and sodium lauryl alkyl sulfate.

Paraffin sulfonate surfactants have the general formula $RSO_3M$, wherein R is a primary or secondary alkyl group containing from about 8 to about 22 carbon atoms (preferably 10 to 18 carbon atoms) and M is an alkali metal, e.g., sodium or potassium. Paraffin sulfonate surfactants and methods for their preparation are well known in the art. They may be prepared, for example, by reaction of hydrocarbons with sulfur dioxide, oxygen and a sulfonation reaction initiator. Alternatively, they may be prepared by reacting an alkene and a sodium bisulfite under suitable radiation or catalysis, as disclosed in British Pat. No. 1,451,228 published Sept. 29, 1976 and hereby incorporated herein by reference. Paraffin sulfonate surfactants are commercially available, e.g., from Farbwerke Hoechst A.G.

Preferred paraffin sulfonates herein are secondary paraffin sulfonates. Examples of specific paraffin sulfonates herein are:

Sodium-1-decane sulfonate;
Potassium-2-decane sulfonate;
Litium-1-dodecane sulfonate;
Sodium-6-tridecane sulfonate;
Sodium-2-tetradecane sulfonate;
Sodium-1-hexadecane sulfonate;
Sodium-4-octadecane sulfonate;
Sodium-3-octadecane sulfonate.

Normally, the paraffin sulfonates are available as mixtures of individual chain lengths and position isomers, and such mixtures are suitable for use herein.

Passive dosing dispensers for immersion in the water contained in the toilet tank of a flush toilet are well known in the prior art. However, such known prior art dispensers are not completely suitable for simultaneously dispensing a disinfectant containing solution, as described earlier herein, in conjunction with a surfactant containing solution, as also described earlier herein, due to the fact that such prior art dispensing apparatus does not maintain the disinfectant containing tablet and the disinfectant containing solution formed by exposing said tablet to water in isolation from the toilet tank water during quiescent periods intermediate flush cycles of the toilet. The same is also true with respect to the surfactant containing tablet and the surfactant containing solution formed by exposing the surfactant containing tablet to water. Without isolation of these active materials from the toilet tank water, and consequently from one another, leaching of the chemicals into the tank and premature mixing of the chemicals with one another results.

Highly improved and effective passive dispensing apparatus capable of providing the desired isolation between the tablet and solution and the surrounding toilet tank water are disclosed in the commonly assigned U.S. patent application of Robert S. Dirksing entitled PASSIVE DOSING DISPENSER, Ser. No. 897,477, filed concurrently herewith and now U.S. Pat. No. 4,171,546, and the commonly assigned U.S. patent application of Robert S. Dirksing entitled PASSIVE DOSING DISPENSER EMPLOYING TRAPPED AIR BUBBLE TO PROVIDE AIR-LOCK, Ser. No. 897,469, filed concurrently herewith and now abandoned, said patent applications being hereby incorporated herein by reference. Improved passive dispensing apparatus of the type generally disclosed in the aforementioned patent application of Robert S. Dirksing provide isolation between the tablet and solution and the toilet tank water by means of air-locks during quiescent periods intermediate flush cycles of the toilet.

It is extremely noteworthy, however, that preferred disinfectant containing tablets employed in practicing the present invention have a quite different dissolution characteristic than the preferred surfactant containing tablets utilized in conjunction with said disinfectant containing tablets. In particular, disinfectant tablets suitable for use in practicing the present invention, when submerged in water, release active ingredients to form an aqueous solution of the disinfectant and soluble inorganic filler/stabilizing salts. Such solubilization results in the formation of a concentration gradient having greatest strength at the bottom of the solution and lowest strength at the surface of the solution. In addition, insoluble salts formed by ion exchange with materials contained in the particular disinfectant containing tablet and undissolved disinfectant particles which tend to break off from the tablet as it dissolves tend to settle to the bottom of the solution.

In dispensing a predetermined quantity of said disinfectant containing solution from a dispensing apparatus of the type generally disclosed in the aforementioned patent applications of Robert S. Dirksing, it is generally preferable to draw from the uppermost surface of the solution, thereby avoiding dispensing the undesirable, corrosion causing particulate materials, i.e., the undissolved solids, collected at the bottom of the solution. Thus, for disinfectant containing solid materials, passive dispenser embodiments of the type generally illustrated in FIGS. 1, 10, 11 and 12 of the aforementioned patent application of Robert S. Dirksing entitled PASSIVE DOSING DISPENSER, Ser. No. 897,477, and now U.S. Pat. No. 4,171,546 and passive dispenser embodiments of the type generally illustrated in FIG. 9 of the aforementioned patent application of Robert S. Dirksing entitled PASSIVE DOSING DISPENSER EMPLOYING TRAPPED AIR BUBBLE TO PROVIDE AIR-LOCK, Ser. No. 897,469, now abandoned are particularly preferred. Drawing FIGS. 1, 10, 11 and 12 of the former application are substantially reproduced herein as FIGS. 1, 10, 11 and 12, respectively, while Drawing FIG. 9 of said latter application is substantially reproduced herein as FIG. 20. A feature common to the aforementioned dispensing embodiments is that the solid disinfectant containing cake is completely immersed within the solution reservoir of the dispenser, and the predetermined quantity of disinfectant containing solution discharged during each flush cycle of the toilet is withdrawn from the uppermost surface of the solution. The undissolved solids contained in the solution reservoir are allowed to settle to the bottom due to gravity, thereby permitting dispensing a predetermined quantity of disinfectant containing solution substantially free of undissolved solids with each flush cycle of the toilet.

Conversely, preferred surfactant containing tablets employed in practicing the present invention form a thick, densified solution when exposed to water for prolonged periods, which densified solution tends to settle to the bottom of the solution reservoir, forming viscosity and concentration gradients between the bottom and the top surfaces of the solution. Accordingly, passive dispensing apparatus which draw from the uppermost surface of the solution and which are generally preferred for use in dispensing a predetermined quantity of disinfectant containing solution generally function with considerably less effectiveness where a surfactant containing solution is involved. This is due to the fact that passive dispensing apparatus of the type preferred for dispensing a disinfectant containing solution in accordance with the present invention generally have insufficient energy to withdraw the thick, densified surfactant containing solution from the lowermost reaches of the reservoir.

Therefore, where a surfactant containing tablet is involved, it is generally desirable to either remove the surfactant containing solution directly from the lowermost reaches of the reservoir, thereby enlisting the assistance of the solution's gravitational head in discharging the viscous solution, or to limit the exposure time between the solid cake or tablet and the liquid solution to substantially prevent the formation of a relatively thick, densified surfactant containing solution. The latter approach may readily be carried out utilizing a dispenser embodiment of the type generally illustrated in FIG. 28 of the commonly assigned U.S. patent application of Robert S. Dirksing entitled PASSIVE DOSING DISPENSER, Ser. No. 897,477, filed concurrently herewith and now U.S. Pat. No. 4,171,546, said Figure being substantially reproduced herein as FIG. 26. In such a dispensing embodiment, the amount of time during which the water contacts the surfactant containing cake is essentially limited to the time interval required to vacuum-transfer a predetermined quantity of water from the measuring cavity and inlet conduit across the lowermost surface of the surfactant containing cake and to collect the solution thus formed in the solution reservoir and discharge conduit. Because the measuring cavity and solution reservoir are of substantially equal volume and are at an elevation lower than the surfactant containing cake, the cake is isolated from the surfactant containing solution once the transfer cycle from the measuring cavity to the solution reservoir of the dispenser has been completed. Accordingly, a relatively thick, densified surfactant containing solution is not formed in the solution reservoir.

Alternatively, passive dispenser embodiments of the type generally illustrated in FIG. 1 and FIG. 15 of the aforementioned commonly assigned U.S. patent application of Robert S. Dirksing entitled PASSIVE DOSING DISPENSER EMPLOYING TRAPPED AIR BUBBLE TO PROVIDE AIR-LOCK, Ser. No. 897,469, filed concurrently herewith and now abandoned, may be employed to dispense a predetermined quantity of surfactant containing solution. Drawing FIGS. 1 and 15 of said application are substantially reproduced herein as FIGS. 35 and 43, respectively. In dispensing embodiments of the latter variety, the portion of the surfactant containing cake exposed to liquid may be controlled by means of a level control partition within the dispenser. In addition, the primary solution reservoir is located at a lower elevation than the surfactant containing cake within the dispenser. Accordingly, the gravitational head of the liquid contained within the dispenser assists in discharging the relatively thick, densified surfactant solution contained within the primary reservoir during each discharge cycle.

Figure 28:
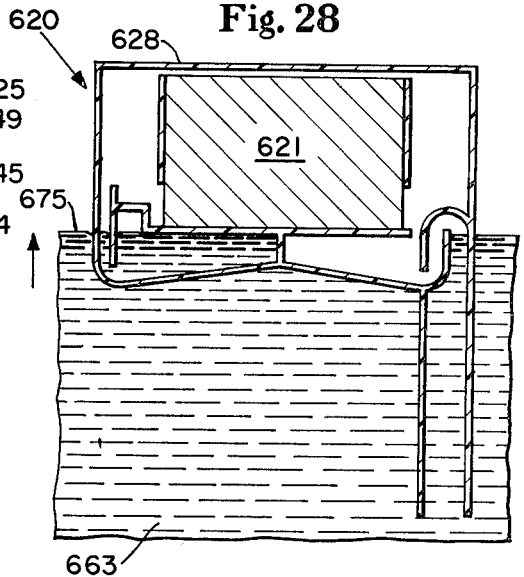

Because a passive dispenser embodiment, as generally illustrated in FIG. 28 of the aforementioned patent application of Robert S. Dirksing entitled PASSIVE DOSING DISPENSER, limits the contact time between the surfactant containing cake and the surfactant containing solution thus formed during quiescent periods intermediate flush cycles of the toilet, the solution discharged during each flush cycle is of substantially constant strength provided only that there is sufficient time for the vacuum-transfer within the dispenser to be carried out intermediate flush cycles of the toilet. Varying the length of the quiescent periods intermediate flush cycles will not affect the strength of solution, since there is no contact between the solution and the surfactant containing cake during such periods once the vacuum-transfer cycle has been carried out. However, in dispensers of the type generally illustrated in FIGS. 1 and 15 of the aforementioned patent application of Robert S. Dirksing entitled PASSIVE DOSING DISPENSER EMPLOYING TRAPPED AIR BUBBLE TO PROVIDE AIR-LOCK, there is prolonged contact between the surfactant containing cake and the liquid solution contained within the dispenser. Accordingly, the strength of the surfactant containing solution discharged from the latter dispensers will be substantially constant when the quiescent periods intermediate flush cycles of the toilet are sufficiently long to permit the solution to become saturated. When the quiescent periods are insufficient for the solution to become saturated, the strength of the surfactant containing solution discharged will still be substantially constant, provided the time periods intermediate said flush cycles are of substantially constant duration.

Referring now to the Figures in which identical features are identically designated, FIG. 1 shows a dispenser 20 suitable for dispensing a disinfectant containing solution in accordance with the present invention. The dispenser 20 contains a solid, water soluble product 21. Dispenser 20 comprises a front wall 22, a back wall 23, two side walls 25 and 26, a top wall 28, a bottom wall 29 (not shown in FIG. 1 but shown in FIGS. 2 through 8 inclusive), interior partitions 31 through 34, and a baffle 36. The walls and partitions are rigid and define a dose-volume measuring cavity 41, an inlet conduit 42, a reservoir 43, and a discharge standpipe 44. Side wall 25 has its top edge designated 51, partition 31 has its bottom edge designated 52, partition 33 has its top edge designated 53, wall 34 has its top edge designated 54, and baffle 36 has its bottom edge designated 55. Baffle 36 also has a beveled front edge 56. In the preferred embodiment dispenser 20, edge 53 is at a higher elevation than edge 54; edge 54 is at a greater elevation than edge 51; and edge 55 is lower than edge 54. The inlet and outlet ports of dispenser 20 are designated 57 and 58 respectively. Together, cavity 41 and conduit 42 form a trap-type inlet.

Figure 2:
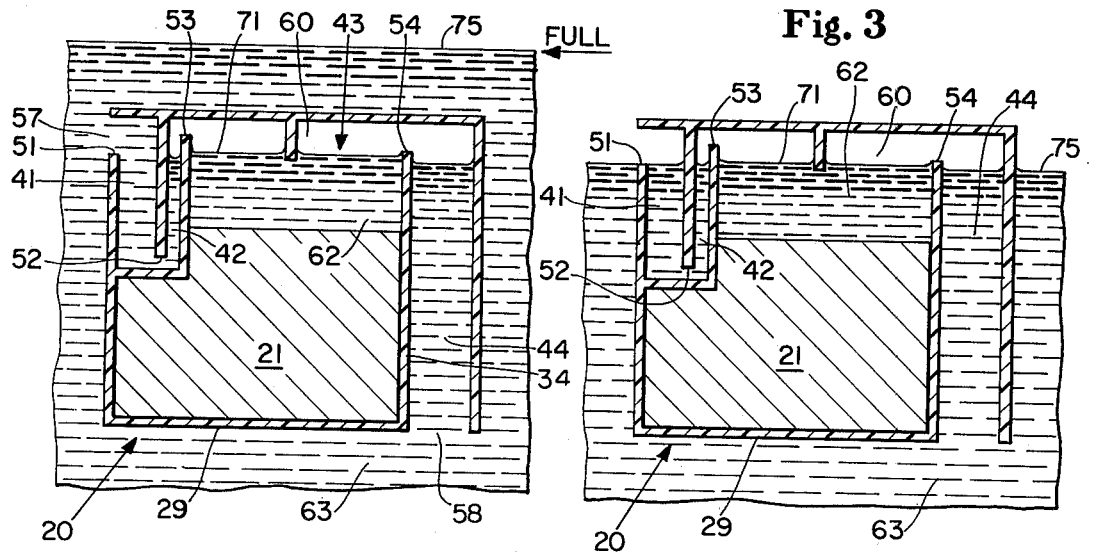
FIGS. 2-8 are simplified sequential sectional views which show a portion of a cycle of the dispenser shown in FIG. 1 and which views are taken along section line 2—2 of FIG. 1.

Briefly, referring to FIG. 2, when a dispenser 20 containing solid product 21 and an aqueous product solution 62 containing solid product 21 and an aqueous product solution 62 is disposed, for instance, in a toilet tank (not shown) on a bracket or other mounting means (not shown) so that the FULL level of water 63 in the toilet tank is sufficiently high to fill the cavity 41, the dispenser will respond as shown in FIGS. 2 through 8 during a toilet flushing cycle as the water drains from the toilet tank. This response causes a dose-volume of water to be vacuum-transferred from cavity 41 and inlet conduit 42 into reservoir 43 via inlet conduit 42, and a dose-volume of product solution 62 to be displaced from reservoir 43 and issue from the dispenser 20 via the discharge standpipe 44 and outlet port 58. As the toilet tank refills, water rises in the discharge standpipe 44 and displaces air therefrom which air exits the dispenser via reservoir 43, inlet conduit 42, and cavity 41 until the cavity 41 is filled through its inlet port 57 with toilet tank water. The air remaining in the dispenser at that time forms an air-lock in the headspace 60 of the reservoir which causes the product 21 and the product solution 62 disposed in reservoir 43 to be isolated from toilet tank water disposed in the inlet conduit 42 and the discharge standpipe 44.

Referring back to FIG. 1, the baffle 36 has its front edge 56 beveled so that it is spaced from the front wall 22 and thereby defines a vent passageway intermediate edge 56 and the adjacent portion of the front wall 22. This vent passageway enables air to pass the baffle 36 as water rises in discharge standpipe 44 while the toilet tank is being refilled with water as described hereinabove; however, the vent passageway is sufficiently small that a rush of air through the headspace 60 of reservoir 43 will, at least in part, be deflected downwardly by baffle 36 as is fully described hereinafter.

Dispenser 20 is preferably provided with a quantity of a dry, solid type product 21 disposed in it as shown in FIG. 1, and may comprise means (not shown) for being secured in a toilet tank at such an elevation that, when the toilet tank is FULL, cavity 41 will be full of toilet tank water. Furthermore, the discharge standpipe 44 is sufficiently long and of sufficient volume that lowering the level of water surrounding the dispenser will cause a sufficient degree of vacuum in the headspace 60 of the dispenser that a predetermined dose-volume of water disposed in cavity 41 will be vacuum-transferred into the reservoir 43 via inlet conduit 42 before the discharge port 58 is uncovered. While a solid mass of product 21 is shown in the Figures, it will be understood from the description contained herein, dispenser embodiments of the type generally illustrated in FIG. 1 may also be utilized to dispense a dose-volume of pre-mixed liquid product solution with each flush cycle of the toilet. In such embodiments, the solid, water soluble product cake is eliminated and the product chamber and solution reservoir are filled with either a pre-mixed liquid product solution or a water soluble powder which dissolves to form a liquid product upon immersion of the dispenser in the toilet tank.

An exemplary embodiment of dispenser 20 has been fabricated from 1.6 mm thick rigid Plexiglas (registered trademark of Rohm & Haas Company) or such. This exemplary embodiment has a height of about 90 mm, a width of about 85 mm, and a thickness of about 20 mm; its edges 51 through 55 are spaced from top wall 28 about 8 mm, 40 mm, 3 mm, 6 mm, and 12 mm, respectively; cavity 41 has a dose-volume of about 6.4 cc; inlet conduit 42 has a cross-section of about 2 mm by 20 mm; and discharge standpipe 44 has a cross-section of about 16 mm by 20 mm. Also, baffle 36 of the exemplary embodiment is disposed about half way between partitions 32 and 34. As is shown in the figures, the top end of inlet conduit 42 (which top end is defined as edge 53 of partition 33) extends to a greater height in the upper reaches of reservoir 43 than the top end of the discharge standpipe 44 (which top end is defined as edge 54 of partition 34). While this exemplary embodiment of dispenser 20 was constructed by adhesively securing sections of Plexiglas to one another, other relatively rigid materials which are substantially inert with respect to the intended product and aqueous solutions thereof can be used to construct dispenser 20. Furthermore, the dispenser could be constructed or formed at high speed and relatively low cost utilizing various manufacturing techniques well known in the art. For example, the dispenser could be vacuum thermoformed in two sections of a material such as polyvinyl chloride having an initial thickness of about 0.020 inches, the solid chemical product 21 inserted therebetween and the two sections thereafter secured to one another as by heat sealing, adhesives, etc. along a line of contact substantially coinciding with section line 2—2 of FIG. 1.

The inlet conduit 42 of the exemplary dispenser 20 described above has a relatively small volume (about 1.4 cc) and a relatively small cross-sectional area so that it will be substantially cleared of water when the headspace 60 is vented via inlet conduit 42 as described hereinafter. However, the cross-sectional area of inlet conduit 42 is sufficiently large to enable a dose-volume of water to be vacuum-transferred from cavity 41 and inlet conduit 42 into reservoir 43 in less than the time which elapses as the level of toilet water 63 recedes from the elevation of edge 51 (the bottom edge of the inlet port 57) to the elevation of the discharge port 58. That is, if the cross-sectional area of inlet conduit 42 presented too great a restriction to flow, incomplete dose-volume transfers would result. Also, the small volume of inlet conduit 42 enables the headspace 60 to be vented therethrough during toilet tank refilling by substantially obviating a deep water trap in the bottom portions of cavity 41 and inlet conduit 42.

In order for dispenser 20 to become functional, reservoir 43 is initially filled with water to form the solution 62, FIG. 2, having its top surface 71 disposed at about the level of the top edge 54 of partition 34. This can be done, for instance, by immersing the dispenser several times in a body of water or by mounting the dispenser in a toilet tank and flushing the toilet several times. Each such immersion or flush will cause a dose-volume of water to be delivered to reservoir 43 from cavity 41. This water will cause a portion of product 21 to dissolve and thereby form the aqueous product solution 62. As is well known to those skilled in the art, dissolution will cease during protracted quiescent periods because the solution 62 will become saturated.

After being placed in operation, the dispenser 20 will, during quiescent periods while the toilet tank is FULL of water 63, be in the state shown in FIG. 2. The top surface 71 of solution 62 will be slightly below top edge 54 of partition 34, and have a concave meniscus adjacent edge 54 as shown. Also, toilet tank water 63 will be disposed in cavity 41, the inlet conduit 42, and the discharge standpipe 44. The level of water in conduit 42 will be about the same as in standpipe 44 which level will be below the top edge 54 of partition 34. This is so because edge 51 is, as stated hereinbefore, at a lower elevation than edge 54. Therefore, when the level of water rises about dispenser 20 during tank refilling, water will flood the cavity 41 through inlet 57 before the level of water in the standpipe 44 reaches edge 54. This causes air to be trapped in the headspace 60 of the reservoir and provides an air-lock which isolates the product 21 and the product solution 62 from the water in the inlet conduit 42 and the discharge standpipe 44.

When the toilet is flushed and the level of water 63 recedes, the top surface 75 of the water first passes top edge 51 of side wall 25 and thereby leaves the cavity 41

Figure 3:
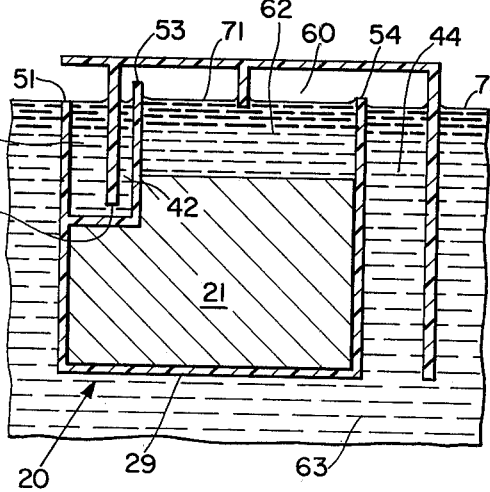
Figure 4:
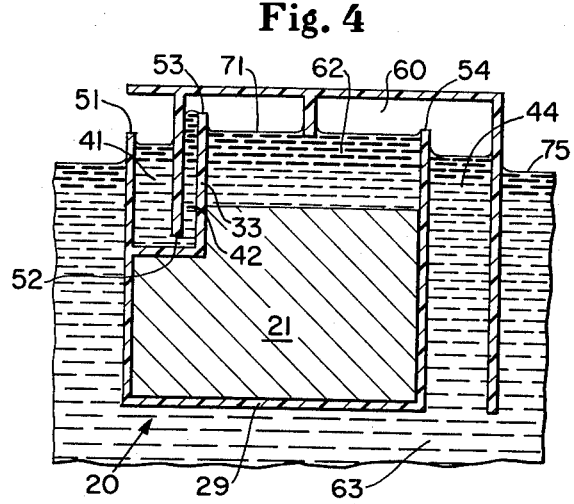
Figure 5:
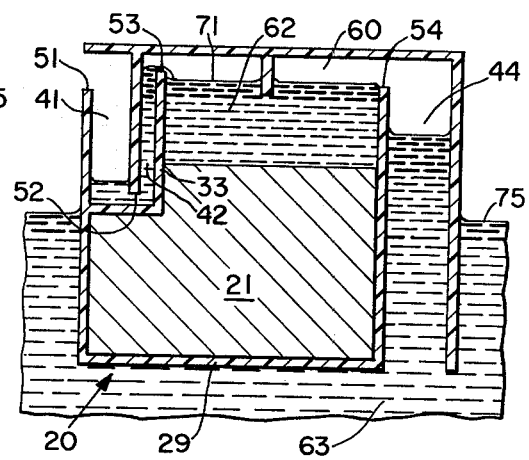
Figure 6:
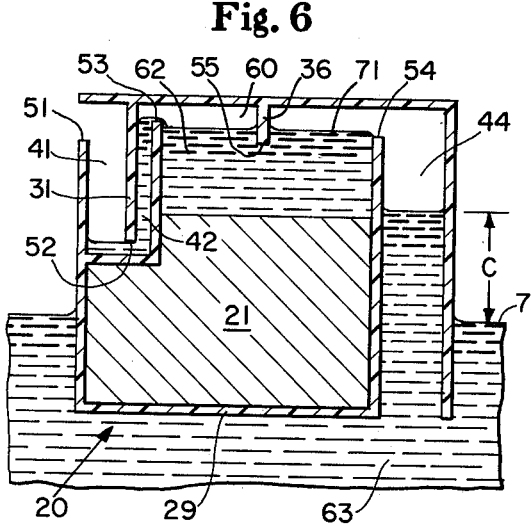
Figure 7:
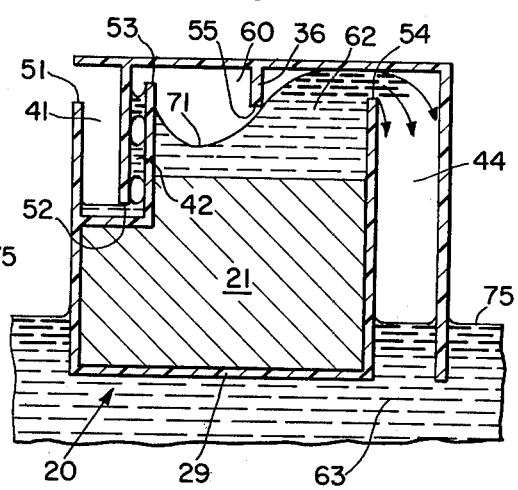
Figure 8:
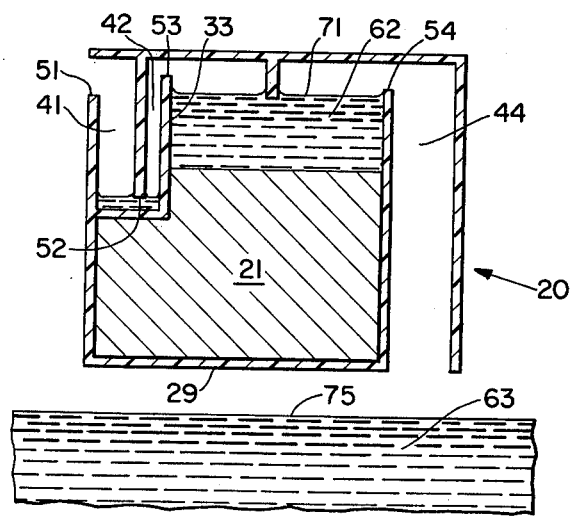

FULL as shown in FIG. 3. As the level of water 63 continues to recede, the top surface 75 thereof passes the level of water disposed in the discharge standpipe 44, FIG. 4 and causes a vacuum to be developed in the headspace 60. This vacuum enables ambient air in the toilet tank to displace water from the cavity 41 into inlet conduit 42. This water then overflows the top edge 53 of partition 33, FIG. 5, and runs down partition 33 and begins to mix with the portion of solution 62 which is disposed adjacent partition 33. This causes the top surface 71 of solution 62 to well up in reservoir 43 and exhibit a somewhat convex meniscus adjacent edge 54 as shown in FIGS. 5 and 6. At the time when the level of water in cavity 41 reaches the elevation of the bottom edge 52 of partition 31, FIG. 6, a column of water is disposed in the discharge standpipe 44 which column extends upwardly a distance "C" from the elevation of the top surface 75 of the receding water 63. Then, air enters the reservoir via inlet conduit 42 and vitiates the vacuum in the headspace 60. This precipitates the collapse of the water column of height "C" in the discharge standpipe 44 which collapse, in turn, precipitates an inrush of air through inlet conduit 42 into the portion of the headspace 60 disposed to the left (as shown in FIG. 7) of baffle 36. This inrush of air is, in part, diverted downwardly because baffle 36 partially obstructs direct flow across the headspace. This diverted air pushes down on the solution 62 disposed to the left of the baffle 36 and the solution 62 displaced thereby, FIG. 7, causes the level of the solution 62 disposed to the right of baffle 36 to rise and flow across partition 34 and down the discharge standpipe. Thus, a dose-volume of solution is virtually blown out of the reservoir 43 as indicated by the arrows in FIG. 7. This induces a tempestuous action in the reservoir which results in mixing the water that has just entered the reservoir with the portion of solution 62 then remaining in the reservoir, and causes the solution to be sufficiently agitated to induce further dissolution of product 21. FIG. 8 shows the dispenser 20 after the tempestuous action has subsided and prior to the rise of water 63. After the dispenser has become immersed by refilling the tank, the state shown in FIG. 2 is resumed and will be maintained while the toilet is in a quiescent state; i.e., until the level of water 63 recedes when the toilet is flushed again.

The dose-volume of dispenser 20 which dose-volume is referred to hereinabove is, essentially, the sum of the partial volumes of both cavity 41 and inlet conduit 42 disposed intermediate the elevation of edges 51 and 52: reference FIG. 3 which shows the dispenser with a dose volume of water disposed in cavity 41 and conduit 42, and FIG. 8 which shows the dispenser after a dose-volume of water has been transferred into reservoir 43 from cavity 41 and conduit 42 in the manner described herein.

Referring back to FIG. 7, were baffle 36 not present, the dispenser would simply issue a dose volume of solution 62 as it is displaced by the incoming dose-volume of make-up water from cavity 41. While this type dispenser would provide a high degree of product and product solution isolation from the tank water during quiescent periods, this type dispenser would not provide the same degree of mixing and agitation in reservoir 43 as compared to dispenser 20 having a baffle 36 or the equivalent thereof. Thus, the baffle 36 comprises means for mixing and agitating liquids disposed in reservoir 43 when a rush of air enters the headspace of the reservoir.

Figure 9:
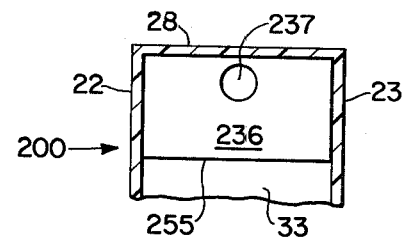
FIG. 9 is a fragmentary sectional view of an alternate embodiment of the dispenser generally illustrated in FIG. 1.

FIG. 9 is a fragmentary sectional view of an alternate embodiment dispenser 200 which view shows an alternate design baffle 236 having a bottom edge 255, and a vent hole 237 through it subjacent the top wall 28. But for these differences, dispenser 200 is identical to dispenser 20. Thus, while a toilet tank in which dispenser 200 is disposed is being filled, air will be displaced from its discharge standpipe and pass through the vent hole 237 in baffle 236 and then exit the dispenser via the inlet conduit of the dispenser in the manner described hereinbefore with respect to dispenser 20. Moreover, the initial filling and the operation of dispenser 200 is also identical to the operation of dispenser 20 as described hereinbefore and therefore will not be repeated.

Figure 10:
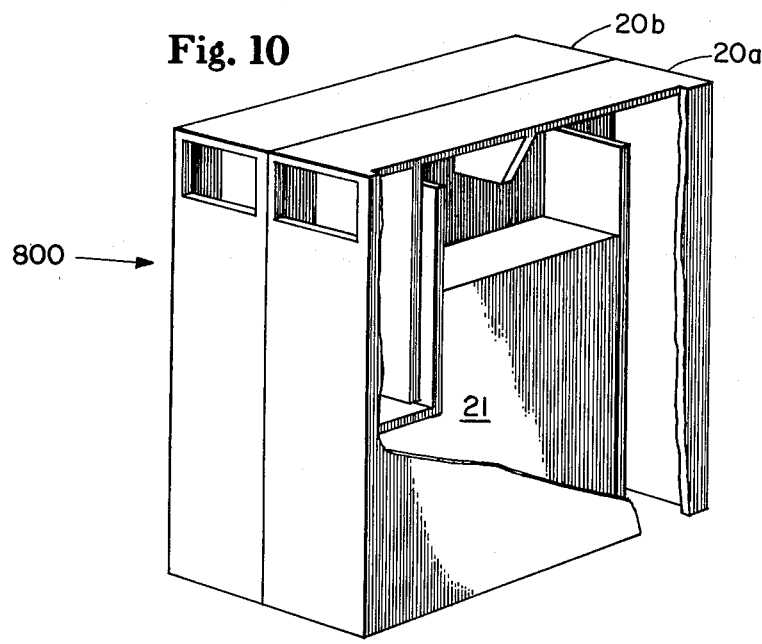
FIG. 10 is a partially torn away perspective view of a dual dispenser embodiment employing a pair of dispensers of the type generally illustrated in FIG. 1 joined to one another along their front and back walls.

FIG. 10 is a partially torn away perspective view of a dual dispenser 800 which dispenser functionally comprises two dispenser sections 20a and 20b such as dispenser 20, FIG. 1, disposed in front-to-back relation. Such dispensers are particularly well suited for plural component products which need to be isolated from each other prior to use. Each dispenser section of such a dual or plural dispenser will maintain a product component in isolation from the toilet tank water and from other product components disposed in other independent sections.

Figure 11:
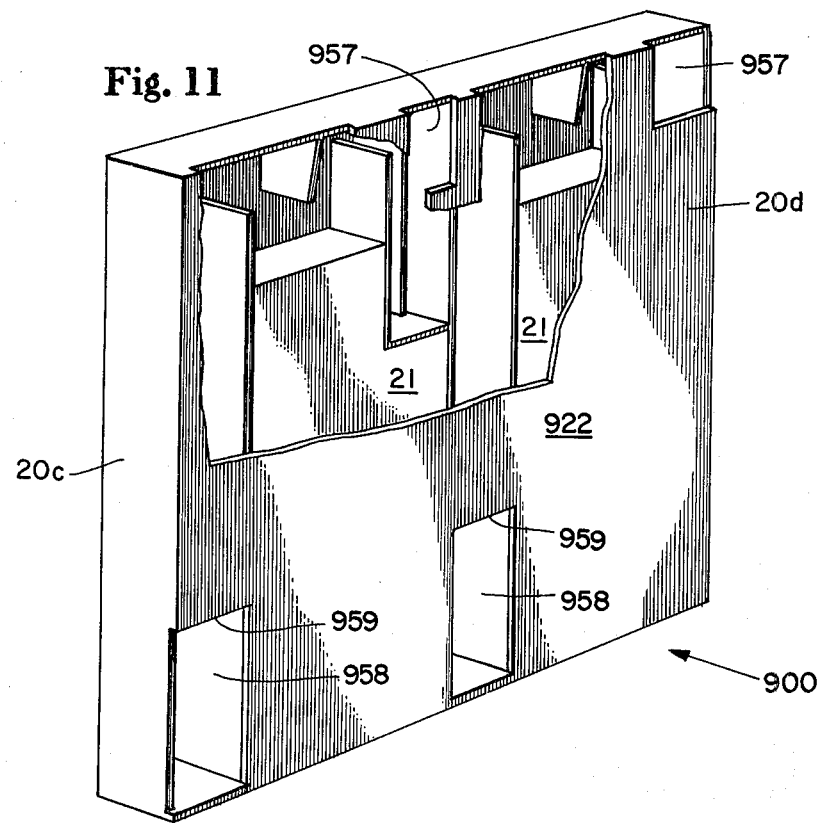
FIG. 11 is a partially torn away perspective view of another dual dispenser embodiment employing a pair of dispensers of the type generally illustrated in FIG. 1 joined to one another along their side walls.

FIG. 11 is a partially torn away perspective view of an alternate embodiment plural section dispenser 900 wherein the plural sections as shown are two in number, are designated 20c and 20d and are disposed in side-by-side relation. Such a dispenser is functionally equivalent to dispenser 800, FIG. 10. However, dispenser 900 is thinner but wider than dispenser 800 and will fit into some toilet tanks which will not accommodate a dispenser 800. Also, the dispenser sections 20c and 20d are provided with two inlet ports 957, and two outlet ports 958 in the unitary front wall 922 rather than in the side and bottom walls as provided in dispenser 20, FIG. 1. While dispenser 900 is shown with its discharge ports spaced apart, it will be obvious that the geometry of dispenser section 22c can be reversed to provide adjacent discharge ports for such purposes as, for instance, enabling better mixing of co-dispensed product solutions. Also, the front discharge enables the dispenser 900 to simply be placed on the bottom wall of toilet tanks which drain sufficiently (i.e.: to below the top edges 959 of the discharge ports 958) rather than being supported in the tank by a bracket or the like.

Referring again to the figures in which identical features are identically designated, FIG. 12 shows an alternative dispenser 120 suitable for dispensing a disinfectant containing solution in accordance with the present invention. The dispenser 120 contains a solid, water soluble product 121. Dispenser 120 comprises a front wall 122, a back wall 123, two side walls 125 and 126, a top wall 128, a bottom wall 129, interior partition 134 and a baffle 136. The embodiment of FIG. 12 differs from the embodiment of FIG. 1 in that the baffle 136 is defined by rigid partitions 131, 133, 181, 182 and 156. The walls and partitions of the dispenser 120 are relatively rigid and define a dose-volume measuring cavity 141, an inlet conduit 142, a product solution reservoir 143, and a discharge standpipe 144. The inlet and outlet ports of dispenser 120 are designated 157 and 158 respectively. The bottom edge of the inlet port 157 is designated 151, partition 131 has its bottom edge designated 152, partition 133 has its top edge designated 153, partition 134 has its top edge designated 154, and the vent passage intermediate the top wall 128 of dispenser 120 and the uppermost partition 156 of baffle 136 is designated 137. In a preferred embodiment of dispenser 120, edge 153 is at a higher elevation than edge 154; edge 154 is at a greater elevation than edge 151; and partition 181 is at a lower elevation than edge 154. Together, cavity 141 and conduit 142 form a trap-type inlet.

Referring to FIG. 13, when a dispenser 120 containing solid product 121 and an aqueous product solution 162 is disposed, for instance, in a toilet tank (not shown) on a bracket or other mounting means (not shown) so that the FULL level of water 163 in the toilet tank is sufficiently high to fill the cavity 141, the dispenser will respond as shown in FIGS. 13–19 during a toilet flushing cycle as the water drains from the toilet tank. This response causes a dose-volume of water to be vacuum-transferred from cavity 141 and inlet conduit 142 into reservoir 143 via inlet conduit 142, and a dose-volume of product solution 162 to be displaced from reservoir 143 and issue from the dispenser 120 via the discharge standpipe 144 and outlet port 158. As the toilet tank refills, water rises in the discharge standpipe 144 and displaces air therefrom which air exits the dispenser via vent passageway 137, inlet conduit 142, and cavity 141 until the cavity 141 is filled through its inlet port 157 with toilet tank water. The air remaining in the dispenser at that time forms an air-lock in the headspace 160 above the reservoir 143, the baffle 136 and the discharge standpipe 144 which causes the product 121 and the product solution 162 disposed in reservoir 143 to be isolated from toilet tank water disposed in the inlet conduit 142 and the discharge standpipe 144.

Referring back to FIG. 12, the uppermost partition 156 of baffle 136 and the uppermost wall 128 of the dispenser 120 define a vent passageway 137 which enables air to pass the baffle 136 as water rises in discharge standpipe 144 while the toilet tank is being refilled with water as described hereinabove. However, the vent passageway 137 is sufficiently small that a rush of air through entry port 157, measuring cavity 141, inlet conduit 142 and the headspace 160 above the right hand portion of reservoir 143 (as shown in FIGS. 12–19) will at least in part be deflected downwardly by baffle 136 in a manner similar to that described in connection with baffle 36 of the dispenser embodiment 20 disclosed in FIG. 1.

The functional design criteria discussed in detail with respect to sizing the various portions of the dispenser embodiment 20 illustrated in FIG. 1, relative to one another, likewise have general application to a dispenser 120 of the type illustrated in FIG. 12.

In order for dispenser 120 to become functional, reservoir 143 is initially filled with water to form the solution 162, FIG. 13, having its top surface 171 disposed at about the level of the top edge 154 of partition 134. As with the embodiment illustrated in FIG. 1, this can be done by immersing the dispenser several times in a body of water or by mounting the dispenser in a toilet tank and flushing the toilet several times. Each such immersion or flush will cause a dose-volume of water to be delivered to reservoir 143 from cavity 141. This water will cause a portion of product 121 to dissolve and thereby form the aqueous product solution 162. Dissolution of the product 121 will cease during protracted quiescent periods because the solution 162 will become saturated.

After being placed in operation, the dispenser 120 will, during quiescent periods while the toilet tank is full of water 163, be in the state shown in FIG. 13. The top surface 171 of solution 162 will be slightly below top edge 154 of partition 134, and have a concave meniscus adjacent edge 154 as shown. Also, toilet tank water 163 will be disposed in cavity 141, the inlet conduit 142, and the discharge standpipe 144. The level of water in conduit 142 will be about the same as in standpipe 144 which level will be below the top edge 154 of partition 134. This is so because edge 151 of entry port 157 is, as stated hereinbefore, at a lower elevation than edge 154. Therefore, when the level of water rises about dispenser 120 during tank refilling, the water will flood the cavity 141 through inlet 157 before the level of water in the standpipe 144 reaches edge 154. This causes air to be trapped in the headspace 160 above the reservoir and standpipe and provides an air-lock which isolates the product 121 and the product solution 162 from the water in the inlet conduit 142 and the discharge standpipe 144.

When the toilet is flushed and the level of water 163 recedes, the top surface 175 of the water first passes edge 151 of inlet port 157 and thereby leaves the cavity 141 FULL as shown in FIG. 14. As the level of water 163 continues to recede, the top surface 175 thereof passes the level of water disposed in the discharge standpipe 144, FIG. 15, and causes a vacuum to be developed in the headspace 160. This vacuum enables ambient air in the toilet tank to displace water from the cavity 141 into inlet conduit 142. This water then overflows the top edge 153 of partition 133, FIG. 16, and begins to mix with the portion of solution 162 which is disposed adjacent partition 133. This causes the top surface 171 of solution 162 to well up in reservoir 143 and exhibit a somewhat convex meniscus adjacent edge 154 as shown in FIG. 16. At the time when the level of water in cavity 141 reaches the elevation of the bottom edge 152 of partition 131, FIG. 17, a column of water is disposed in the discharge standpipe 144 which column extends upwardly a distance "D" from the elevation of the top surface 175 of the receding water 163. Passageway 137 is at least partially blocked at this point in the cycle by liquid attempting to move to the left hand side of the dispenser, and product solution 162 is beginning to overflow edge 154. Then, air enters the reservoir 143 via inlet port 157, measuring cavity 141 and inlet conduit 142 and vitiates the vacuum in the headspace 160. This precipitates collapse of the water column of height "D" in the discharge standpipe 144, which collapse, in turn, precipitates an inrush of air through inlet conduit 142 into the portion of the headspace 160 disposed to the right (as shown in FIG. 18) of baffle 136. This inrush of air is, in part, diverted downwardly because baffle 136 partially obstructs direct flow across the headspace. Furthermore, the small size of passageway 137 which is at least partially blocked by water, FIG. 18, causes the inrushing air to take the path of least resistance, i.e., downwardly into solution reservoir 143, thereby virtually blowing a dose-volume of solution 162 out of the reservoir 143 as indicated by the arrows in FIG. 18. This induces a tempestuous action in the reservoir 143 which results in mixing the water that has just entered the reservoir with the portion of solution 162 then remaining in the reservoir, and causes the solution to be sufficiently agitated to induce further dissolution of solid product 121. FIG. 19 shows the dispenser 120 after tempestuous action has subsided and prior to the rise of water 163. After the dispenser has become immersed by refilling the tank, the state shown in FIG. 13 is resumed and will be maintained while the toilet is in a quiescent state, i.e., until the level of water 163 recedes when the toilet is flushed again.

The dose-volume dispenser 120 which dose-volume is referred to hereinabove is, essentially, the sum of the partial volumes of both cavity 141 and inlet conduit 142 disposed intermediate the elevation of edge 151 of entry port 157 and edge 152 of partition 131. Note FIG. 14 which shows the dispenser with a dose-volume of water disposed within cavity 141 and conduit 142, and FIG. 19 which shows the dispenser after a dose-volume of water has been transferred into reservoir 143 from cavity 141 and conduit 142 in the manner described herein.

As has been pointed out with respect to the embodiment illustrated in FIG. 1, were baffle 136 not present in the embodiment illustrated in FIG. 12, the dispenser would simply issue a dose-volume of solution 162 as it is displaced by the incoming dose-volume of makeup water from cavity 141. While such a dispenser would provide a high degree of product and product solution isolation from the tank water during quiescent periods, it would not provide the same degree of mixing and agitation in reservoir 143 as compared to dispenser 120 having a baffle 136 or the equivalent thereof. Thus, the baffle 136 comprises means for mixing and agitating liquids disposed in reservoir 143 when a rush of air enters the headspace 160 of the reservoir.

An exemplary embodiment of dispenser 120 has been fabricated from 1.6 millimeter thick rigid Plexiglas (Registered trademark of Rohm & Haas Company) or such. This exemplary embodiment has a height of about 90 millimeters, a width of about 90 millimeters, and a thickness of about 20 millimeters; its edges 151-154 are spaced from the top wall 128 about 12 millimeters, 22 millimeters, 8 millimeters and 10 millimeters, respectively; partition 181 is spaced approximately 28 millimeters from top wal 128; cavity 141 has a dose-volume of about 8 cubic centimeters; inlet conduit 142 has a cross-section of about 2 millimeters by about 20 millimeters; and discharge standpipe 144 has a cross-section of about 16 millimeters by about 20 millimeters. Also, baffle 136 of the exemplary embodiment illustrated in FIG. 12 is disposed about half way between dispenser wall 125 and partition 134 and measures approximately 50 millimeters in width and 25 millimeters in height. Passageway 137 has a cross-section of about 2 millimeters by about 20 millimeters, while entry port 157 has a height of approximately 5 millimeters and a width of approximately 40 millimeters. As is shown in FIGS. 12-19, the top end of inlet conduit 142 (which top end is defined as edge 153 of partition 133) extends to a greater height in the upper reaches of reservoir 143 than the top end of the discharge standpipe 44 (which top end is defined as edge 154 of partition 134). While the exemplary embodiment of the dispenser 120 was constructed by adhesively securing sections of Plexiglass to one another, other relatively rigid materials which are substantially inert with respect to the intended product and aqueous solutions thereof can be used to construct dispenser 120. For example, a dispenser having the desired passageways could be vacuum thermoformed in two sections of a material such as polyvinyl chloride having an initial thickness of about 0.020 inches, the solid chemical 121 inserted therebetween and the two sections thereafter secured to one another as by heat sealing, adhesives, etc. along a line of contact substantially coinciding with section line 13-13 of FIG. 12.

A dispenser 120 of the type generally illustrated in FIG. 12 permits the use of a symmetrically shaped, solid, water soluble product 121, increases the surface exposure of the solid product to the product solution 162, and improves the flow of incoming toilet tank water 163 across the solid product. Since the width to depth ratio of the solid product 121 is increased with the arrangement illustrated in FIG. 12 when compared to the arrangement illustrated in FIG. 1, agitation of the product solution 162 by the incoming water to the lower reaches of the dispenser chemical chamber, i.e., the lowermost portions of reservoir 143, is also improved.

Figure 20:
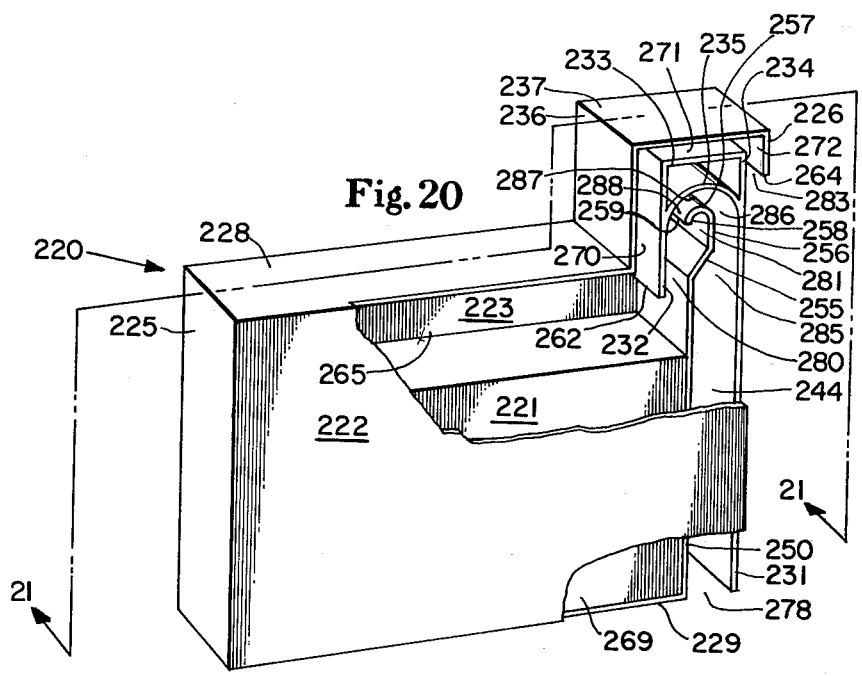
FIG. 20 is a partially torn away perspective view of yet another embodiment of a passive dosing dispenser suitable for dispensing a disinfectant containing solution in accordance with the present invention.

FIG. 20 illustrates yet another embodiment of a dispenser 220 suitable for dispensing a disinfectant containing solution in accordance with the present invention. Dispenser 220 comprises a front wall 222, a back wall 223, sidewall segments 225, 226, 231 and 236, top wall segments 228 and 237, bottom wall 229, interior partition segments 232, 233, 234, 235, 250, 255, 256, 257 and 258. The wall segments and partition segments are relatively rigid and define a syphon tube 244 having inlet/-discharge port 278 at its lowermost end and sections 285 and 286 at its uppermost end, a horizontal passageway 287, a vertical passageway 288 connecting with inlet/-discharge conduit 280, said inlet/discharge conduit having an air trap 281 disposed adjacent thereto in a manner similar to that of dispenser embodiment 20' illustrated in FIG. 35, a solid product chamber 269, a product solution reservoir 265 and vent passageways 270, 271 and 272 connecting said solid product chamber and said solution reservoir with air vent 283 which coincides with edge 264 of sidewall segment 226. Lowermost edge of partition segment 232 is designated 262 and lowermost edge of partition segment 258 is designated 259. While a solid, water soluble product cake 221 is disposed within the lowermost portions of reservoir 265, it will be understood from the description contained herein, dispenser embodiments of the type generally illustrated in FIG. 20 may also be utilized to dispense a dose-volume of pre-mixed liquid product solution with each flush cycle of the toilet. In such embodiments, the solid, water soluble product cake is eliminated and the product chamber and solution reservoir are filled with either a pre-mixed liquid product solution or a water soluble powder which dissolves to form a liquid product solution upon immersion of the dispenser in the toilet tank.

Figure 21:
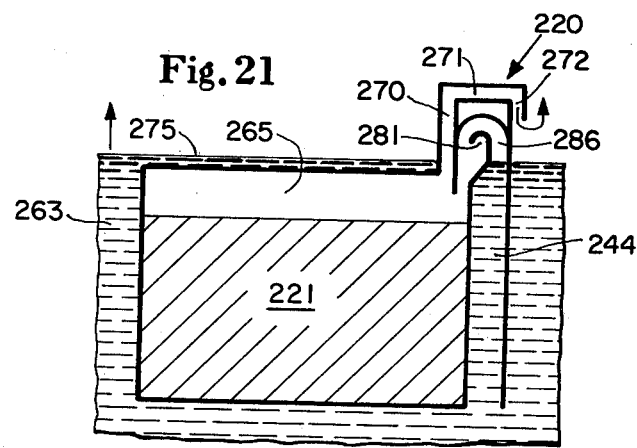
FIGS. 21-25 are simplified, sequential sectional views which show a portion of a cycle of the dispenser shown in FIG. 20 and which views are taken along section line 21—21 of FIG. 20.
Figure 22:
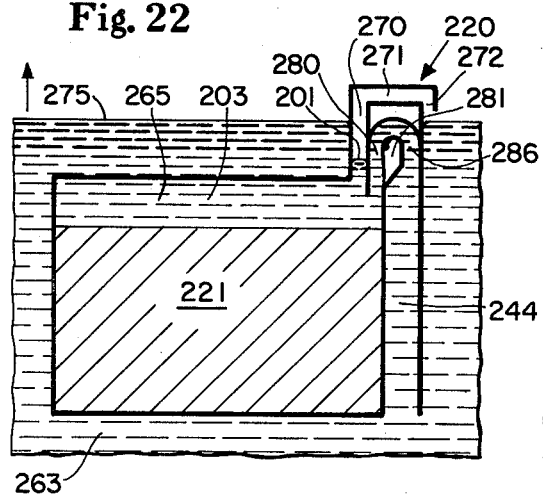
Figure 23:
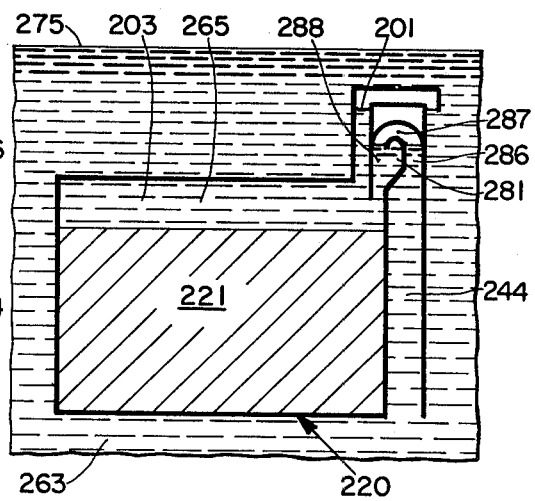

The principles of operation of dispenser 220 illustrated in FIG. 20 are, with the obvious exception of relocation of the solid product 221 to the lower position, generally the same as those hereinafter described in connection with dispenser embodiment 20' of FIG. 35. As shown in FIG. 21, the water level 275 is rising in the toilet tank and in syphon tube 244. In the condition illustrated in FIG. 21, the dispenser 220 has not yet been completely immersed in the toilet tank. Consequently, solution reservoir 265 is at this point devoid of product solution. As toilet tank water 263 rises in syphon tube 244, air is vented through passageways 285, 286, 287 and 288, inlet/discharge conduit 280, solution reservoir 265 and passageways 270, 271 and 272 to air vent 283. As shown in FIG. 22, when water traverses horizontal passageway 287, vertical passageway 288 and enters reservoir 265 via inlet/discharge conduit 280, an air bubble is retained within air trap 281 in a manner similar to that described in connection with dispenser embodiment 20' of FIG. 35. Toilet tank water entering solution reservoir 265 begins to dissolve the solid product 221 to form an aqueous product solution 203. The level 201 of solution 203 continues to rise in passageway 270 until such time as the toilet tank water level blocks air vent 283, at which point water ceases to flow into dispenser 220 via syphon tube 244. FIG. 23 depicts the condition of dispenser 220 when the water in the toilet tank has reached the FULL level and the dispenser has been fully charged with toilet tank water to form product solution 203. When the water ceases to flow in horizontal passageway 287 and vertical passageway 288, the bulk of the air bubble retained in air trap 281 rises and in so doing rotates about edge 259 of partition segment 258 to form an air-lock in horizontal passageway 287 and the uppermost segments of vertical passageways 286 and 288, as shown in FIG. 23. The condition shown in FIG. 23 will persist during quiescent perios intermediate flush cycles of the toilet.

Figure 24:
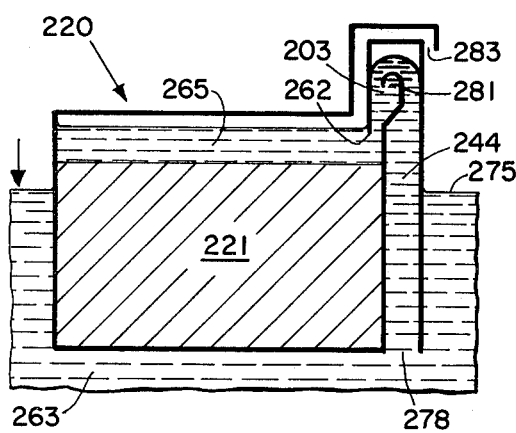

When the toilet is flushed, FIG. 24, water in the toilet tank will fall below air vent 283 of dispenser 220. This provides an air supply so that syphoning of the product solution 203 from reservoir 265 may occur. As shown in FIG. 24, air trap 281 is filled with product solution 203 as the syphoning action from the reservoir 265 to syphon tube 244 takes place. The syphoning action will continue until such time as the solution level 201 reaches lowermost edge 262 of partition segment 270, at which time the column of liquid retained in syphon tube 244 is vented and allowed to discharge into the toilet tank through inlet/discharge port 278.

Figure 25:
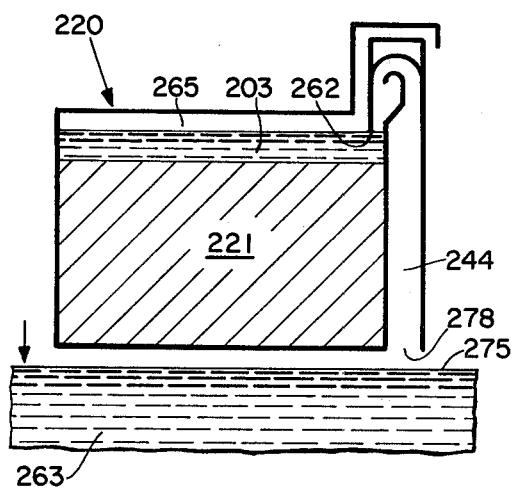

After the toilet tank water has dropped beneath inlet/discharge discharge port 278, FIG. 25, a quantity of product solution 203 remains within solution reservoir 265 at a level approximating that of lowermost edge 262 of partition segment 270. The solution remaining within dispenser 220 serves as a buffer in providing solution for rapid multiple flushes. When the level of toilet tank water rises again, dispenser 220 will once more be restored to the condition illustrated in FIG. 23.

Figure 26:
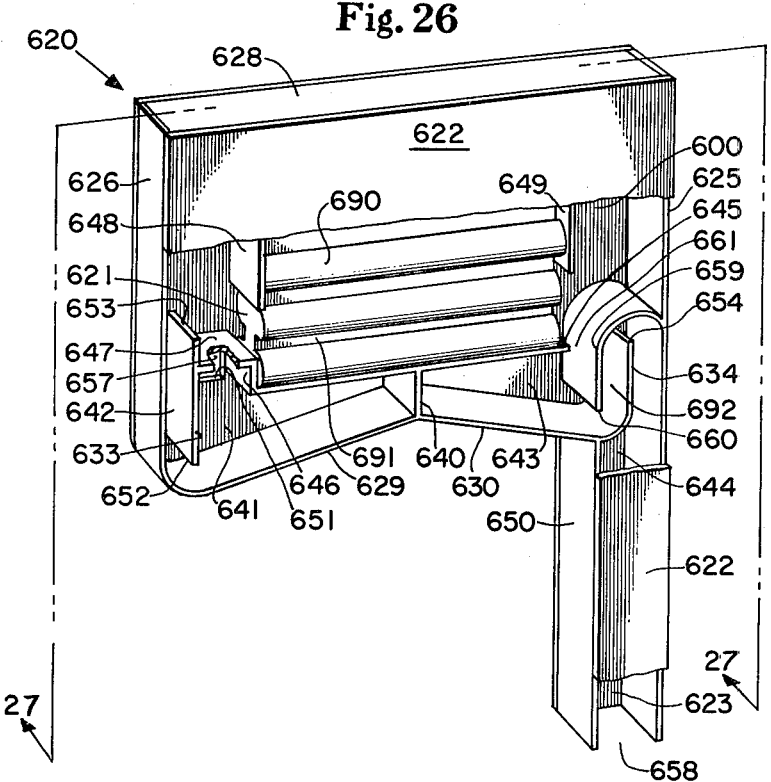
FIG. 26 is a partially torn away perspective view of an embodiment of a passive dosing dispenser suitable for dispensing a surfactant containing solution in accordance with the present invention.

FIG. 26 discloses a dispenser embodiment 620 suitable for dispensing a surfactant containing solution in accordance with the present invention, said dispenser containing a solid, water soluble product 621. Dispenser 620 comprises a front wall 622, a back wall 623, side wall segments 625, 626 and 650, a top wall 628, bottom wall segments 629 and 630, interior partitions 633, 634, 640, 645, 646, 647, 659 and product-restraining partitions 648 and 649. The embodiment of FIG. 26 differs from other dispenser embodiments described herein in that the product solution 662 does not contact the solid product 621 during quiescent periods. The walls and partitions of the dispenser are relatively rigid and define a dose-volume measuring cavity 641, and inlet conduit 642, a product solution reservoir 643, a discharge conduit 692 and discharge standpipe 644. In a particularly preferred embodiment, the dose-volume measuring cavity 641 and inlet conduit 642 are of substantially equal volume to the product solution reservoir 643 and discharge conduit 692 respectively. The inlet and outlet ports of dispenser 620 are designated 657 and 658 respectively. The bottom edge of the inlet port 657 is designated 651, partition 633 has its bottom edge designated 652 and its top edge designated 653, partition 634 has its top edge designated 654, and partition 659 has its bottom edge designated 670. The entrance passageway into reservoir 643 is designated 661. In a preferred embodiment of dispenser 620, edge 653 is at a higher elevation than edge 654; edge 654 is at a higher elevation than edge 651 of inlet port 657; and the uppermost reaches of measuring cavity 641 and product solution reservoir 643 are at a lower elevation than solid product 621. The solid product 621 utilized in dispenser 620 is so configured as to permit the horizontal passage of air across its surface between the inlet and discharge ports 657 and 658 respectively. In the illustrated embodiment, this is provided by means of raised segments 690 which form longitudinally extending valley segments 691 intermediate the raised segments along opposite surfaces of the solid product. As the solid product 621 is consumed by water erosion, it settles by gravity against partition segment 645. Measuring cavity 641 and inlet conduit 642 form a trap-type inlet, whle solution reservoir 643, discharge conduit 692 and partition 659 form an inverted trap-type outlet.

Figure 27:
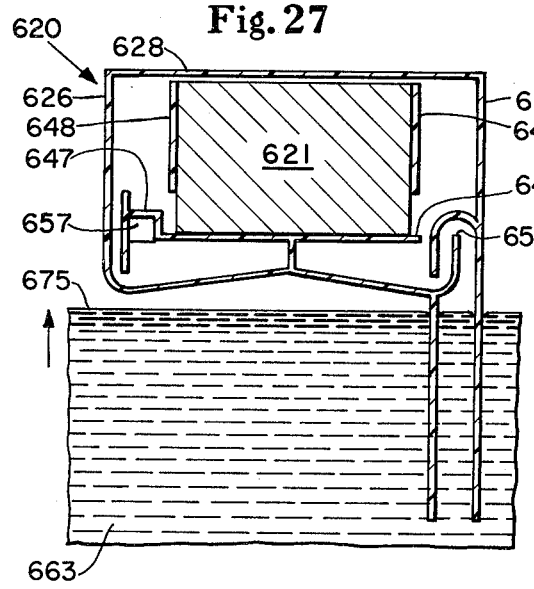

Referring to FIG. 27, a dispenser 620 containing solid product 621 is initially disposed, for instance, in a toilet tank (not shown) on a bracket or other mounting means (not shown) and the level of water 663 in the toilet tank is permitted to rise, as after a flush cycle. FIGS. 28–34 illustrate a pair of consecutive flush cycles which place the dispenser 620 in operation. In normal operation, a dose-volume of water is vacuum-transferred from cavity 641 and inlet conduit 642 across the lowermost surface of solid product 621 and into solution reservoir 643 and discharge conduit 692. Once the product solution reservoir 643 and discharge conduit 692 have been filled with product solution 662, each flush cycle of the toilet will cause a dose-volume of the product solution to issue from the dispenser 620 via the discharge standpipe 644 and outlet port 658. As the toilet tank refills, water rises in the discharge standpipe 644 and displaces air therefrom, which air exits the dispenser via discharge conduit 692, product solution reservoir 643, passageway 661, inlet conduit 642, and dose-volume measuring cavity 641 until the cavity 641 is filled through its inlet port 657 with toilet tank water. The air remaining in the dispenser at that time forms an air-lock in the headspace 600 in the uppermost regions of the solid product chamber (FIG. 32). In addition, an air-lock is formed in the headspace 698 adjacent the uppermost regions of discharge conduit 692 and discharge standpipe 644 (FIG. 32). The air-lock formed in the headspace 698 isolates the product solution 662 in the reservoir 643 and discharge conduit 692 from the toilet tank water in the discharge standpipe 644 while the air-lock formed in the headspace 600 in the uppermost regions of the dispenser isolates the solid product 621 from the toilet tank water disposed in the inlet conduit 642.

Because the volume of reservoir 643 and discharge conduit 692 are substantially equal to the volume of measuring cavity 641 and inlet conduit 642 respectively, the toilet tank water drawn across the lowermost surface of the solid product cake 621 during the flushing cycle is completely collected within the confines of reservoir 643 and discharge conduit 692, thereby isolating the solid product 621 from the product solution 662.

In general, the functional design criteria discussed in detail with respect to sizing the various portions of the dispenser embodiment illustrated in FIG. 1, relative to one another, are likewise applicable to a dispenser 620 of the type illustrated in FIG. 26.

FIG. 27 depicts the condition of a dispenser 620 prior to being filled with water by immersion in a toilet tank. Water continues to rise, FIG. 28, until it flows through inlet port 657 in the back wall 623 of the dispenser. As water enters the dose-volume measuring cavity 641, water rising in the discharge standpipe 644 ceases to rise since the air is no longer able to vent through discharge conduit 692, reservoir 643, passageway 661, across the surfaces of solid product 621, down inlet conduit 642 and out cavity 641 to entry port 657. Because the air vent is closed, air is trapped in the upper reaches or headspace 600 of the solid product chamber as well as in product solution reservoir 643, discharge conduit 692 and headspace 698 adjacent the upper reaches of discharge conduit 692 and discharge standpipe 644. Thus, FIG. 29 represents the condition of the dispenser during a quiescent period awaiting the first flush cycle of the toilet after toilet tank water 663 has risen to a FULL level 675 sufficient to block the entry port 657 of the dispenser 620. FIG. 30 represents the condition of the dispenser 620 after the toilet has been flushed and the water level in the tank has begun to drop. As the water in the discharge standpipe 644 attempts to fall, a partial vacuum is created which draws water from the inlet conduit 642 and dose-volume measuring cavity 641 across edge 653 of partition 633 and into contact with the left side (as shown in FIG. 30) of solid product 621. Because the solid product 621 offers at least a degree of resistance to the flow of water coming across its lowermost surface, it is desirable that the uppermost edge 653 of partition 633 be sufficiently high that the dose-volume of water drawn from inlet conduit 642 and measuring cavity 641 is substantially prevented from reentering inlet conduit 642 when the water level in measuring cavity 641 reaches the lowermost edge 652 of partition 633 and the partial vacuum is broken. As can be seen in FIG. 31, the fresh water transferred from the measuring cavity 641 and inlet conduit 642 slowly trickles across the base of the solid product 621 and dissolves the same to form a liquid solution 662. This solution enters reservoir 643 through passageway 661. The product solution 662 thus accumulated in reservoir 643 and discharge conduit 692 becomes available for the next flush cycle of the toilet.

FIG. 32 depicts the condition of the dispenser 620 when it is ready to dispense product solution 662 contained in reservoir 643 and discharge conduit 692. It should be noted that the inverted trap-type outlet in the upper reaches of discharge conduit 692 and discharge standpipe 644 creates a secondary air-lock in the headspace 698 associated therewith. This secondary air-lock provides isolation between the product solution 662 and the toilet tank water 663 in discharge standpipe 644.

Figure 33:
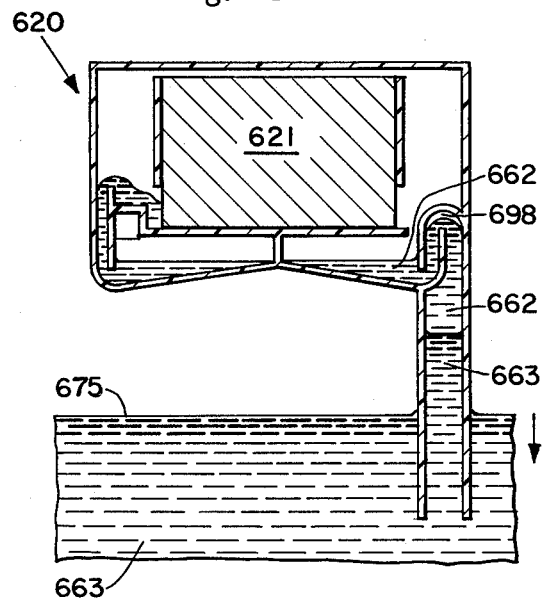

FIG. 33 depicts the condition of the dispenser 620 when vacuum-transfer of product solution 662 contained in reservoir 643 and discharge conduit 692 has been initiated by the falling level of toilet tank water. This produces a corresponding vacuum-transfer of fresh water from measuring cavity 641 and inlet conduit 642 across the lowermost surfaces of the solid product 621. When the level of water in measuring cavity 641 reaches the lowermost edge 652 of partition 633, FIG. 34, air is permitted to vent via inlet port 657, measuring cavity 641, inlet conduit 642, across the surface of the solid product 621, through passageway 661 and out reservoir 643 and discharge conduit 692, thereby venting the column of toilet tank water 663 and product solution 662 in discharge standpipe 644. The column of liquid contained in discharge standpipe 644 is thereby completely discharged into the toilet tank. Meanwhile the fresh water solution drawn from measuring cavity 641 and inlet conduit 642 trickles across the lowermost surfaces of the solid product cake 621 and finds its way into reservoir 643 and discharge conduit 692 so as to be available for the next flush cycle. The downward slope of the product solution reservoir bottom wall 630 in the direction of discharge conduit 692 promotes emptying of the reservoir during the vacuum-transfer portion of the cycle.

Figure 34:
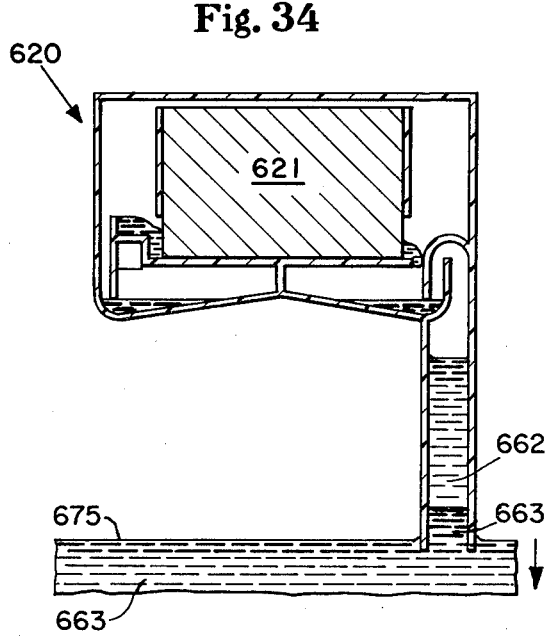

A dispenser 620 of the type generally illustrated in FIG. 26 offers isolation not only of the toilet tank water 663 from the solid product 621 and the product solution 662, but also isolation between the solid product 621 and the product solution 662 during quiescent periods. In addition, because the product solution 662 has already entered the discharge standpipe 644 when the vacuum is broken, as shown in FIG. 34, the discharge of product solution is very complete and very rapid. Furthermore, it is near the end of the flush cycle. The former feature provides good dispersion of the product solution 662 in the toilet tank water, while the latter feature ensures that more of the product solution dispensed during each flush cycle will be retained in the bowl after the flush cycle has been completed, and thus will be at a higher concentration than if it were dispensed during the early portions of the flush cycle. This is so because of the inherent operation of a flushing toilet. Generally all the water from the toilet tank goes through the toilet bowl. However, the initial portions of water are used to initiate a syphon action which carries away the waste material, while the latter portions are used to refill the toilet bowl. By dispensing the product solution into the latter discharged portions of the tank water a higher solution concentration in the toilet bowl is provided intermediate flush cycles. If the product solution were dispensed into the initially discharge portions of the toilet tank water, a large portion of the solution would be carried away with the waste material so that the concentration of solution remaining in the toilet bowl would be greatly reduced.

The dose-volume of product solution 662 dispensed during each flush cycle by dispenser 620 is, essentially, the sum of the partial volumes of both cavity 641 and inlet conduit 642 disposed intermediate the elevation of edge 651 of inlet port 657 and edge 652 of partition 633.

An exemplary embodiment of dispenser 620 has been fabricated from 1.6 millimeter thick rigid Plexiglas (Registered Trademark of Rohm & Haas Company) or such. This exemplary embodiment has an overall height of about 75 millimeters excluding the height of discharge standpipe 644 which extends below wall segment 630 a distance of approximately 75 millimeters, an overall width of approximately 125 millimeters and an overall depth of approximately 20 millimeters. The centrally located solid product 621 has a length of approximately 75 millimeters, an initial height of approximately 50 millimeters and a maximum depth of approximately 20 millimeters. Edge 653 measures approximately 40 millimeters, edge 652 approximately 64 millimeters, edge 651 of entry port 657 approximately 55 millimeters, partition segment 647 approximately 45 millimeters, partition segment 645 approximately 50 millimeters, edge 660 approximately 62 millimeters, edge 654 approximately 50 millimeters, and the uppermost portion of partition 659 approximately 45 millimeters from top wall 628. Passageway 661 measures approximately 5 millimeters by approximately 20 millimeters. Discharge standpipe 644 has a cross-section of approximately 8 millimeters by approximately 20 millimeters, discharge conduit 692 a cross-section of approximately 3 millimeters by approximately 20 millimeters, and inlet conduit 642 a cross-section of approximately 3 millimeters by approximately 20 millimeters. Measuring cavity 641 and product solution reservoir 643 each have a volume of approximately 8 cubic centimeters. While this exemplary embodiment of dispenser 620 was constructed of Plexiglas segments adhesively bonded to one another, other relatively rigid materials and fabrication techniques well known to those skilled in the art may be utilized to construct a dispenser 620 of the type generally illustrated in FIG. 26.

Referring again to the Figures in which identical features are identically designated, FIG. 35 shows a dispenser 20' suitable for dispensing a surfactant containing solution in accordance with the present invention and containing a solid, water soluble product 21'. Dispenser 20' comprises a front wall 22', a back wall 23', sidewall segments 25', 26', 31', 50', 51', 52' and 90', a top wall 28', bottom wall segments 29', 53' and 54', and interior partitions 32', 33', 55', 56', 57', 58', 91', 95' and 96'. The walls and partitions are rigid and define a primary product reservoir 65', a secondary product reservoir 68', a solid product chamber 69', a syphon tube 44' having uppermost vertical passageways 85' and 86', a horizontal passageway 87', a vertical passageway 88' connecting with inlet/discharge conduit 80', said inlet/discharge conduit having an air trap 81' disposed adjacent thereto, and vent means for the product chamber comprising passageways 71' and 72' and air vent 83'. The lowermost edge of partition segment 58' is designated 59', the lowermost edge of partition segment 96' is designated 67', the uppermost edge of partition segment 33' is designated 61', the lowermost edge of level control partition 32' is designated 62', the uppermost edge of sidewall segment 31' is designated 93', and the lowermost edge of sidewall segment 26', which in conjunction with front and back walls 22' and 23' respectively and sidewall segment 31' define air vent 83+, is designated 64'. The inlet/discharge port of dispenser 20' located at the lowermost end of syphon tube 44' is designated 78'.

Briefly, referring to FIG. 26 and dispenser 20' containing solid product 21' is disposed, for instance, in a toilet tank (not shown) on a bracket or other mounting means (not shown) so that the FULL level of water 63' in the toilet tank is sufficiently high to at least reach edge 64' of sidewall segment 26', the dispenser will respond as shown in FIGS. 36–42 as the level of water rises to the FULL position in the toilet tank and the toilet is transfer flushed.

The dispenser 20' illustrated in FIG. 35 is shown prior to immersion in the toilet tank water 63'. As the toilet tank water 63' rises, it enters syphon tube 44' through inlet/discharge port 78'. Air within the upper reaches of the syphon tube is allowed to vent through vertical passageways 85' and 86', horizontal passageway 87', vertical passageway 88', inlet/ discharge conduit 80', primary solution reservoir 65', vent passageways 71' and 72' and air vent 83'. As the level of the toilet tank water 63' continues to rise, FIG. 37, it begins to enter horizontal passageway 87'. Because the difference in elevation of the water in the toilet tank and the water within the syphon tube is relatively small prior to air vent 83' becoming blocked, the water head or water pressure available to force the water in syphon tube 44' around the loop through vertical passageway 88' and into inlet/discharge conduit 80' is likewise quite small. To minimize the required driving force to initiate water flow through the loop, the dispenser 20' preferably employs a series of passageways 85', 86', 87' and 88', each of which is smaller in cross-section than any portion of the one immediately preceding it, thereby providing capillary suction in the direction of flow which tends to draw the water from the syphon tube 44' into the inlet/discharge conduit 80'. This feature is more clearly illustrated in the enlarged fragmentary view of FIG. 38. It is of course recognized that a maximum degree of capillary suction may be provided by employing passageways 86', 87' and 88' having characteristics similar to passageway 85' which exhibits a continual reduction in cross-section in the direction of liquid flow during the dispenser charging operation. If desired, the entire length of the syphon tube 44' may be convergent in the direction of water flow during the charging operation.

Once toilet tank water 63' enters inlet/discharge conduit 80' and begins to collect in primary solution reservoir 65', the condition illustrated in FIG. 28 prevails in the air trap 81' disposed adjacent inlet/discharge conduit 80'. Namely, an air bubble is retained within the confines of the air trap 81' defined by partition segments 55', 56', 57' and 58'. The condition illustrated in FIG. 38 persists as long as toilet tank water 63' continues to enter the dispenser 20'.

When the level 101' of solution 103' formed by dissolution of solid product 21' in the incoming water within dispenser product chamber 69' reaches lowermost edge 62' of level control partition 32', an air-lock is formed in the uppermost reaches of the product chamber 69', thereby preventing the solution level 101' from rising further within the product chamber. It should be noted, however, that the solution level 102' in passageway 71' continues to rise until such time as the toilet tank water 63' contacts lowermost edge 64' of sidewall segment 26' and blocks air vent 83', thus providing a secondary air-lock in the uppermost reaches of passageway 71' and passageway 72'. This secondary air-lock isolates the product solution 103' formed by a dissolution of the solid product 21' in the toilet tank water introduced during the charging cycle and the toilet tank water blocking air vent 83'. As is apparent from FIG. 39, the level 102' of product solution 103' within dispenser passageway 71' is identical to the level of toilet tank water 63' in passageway 72'. While the level 102' of product solution 103' in passageway 71' is distinct from the level 101' of the product solution within product chamber 69' due to the presence of level control partition 32' in the illustrated embodiment, it should be noted that level control partition 32' could be eliminated from the dispenser 20' without adversely affecting the basic functioning thereof. However, the level of product solution within the product chamber 69' would then be controlled exclusively by the vertical location of air vent 83'.

As is also apparent from FIG. 39, which represents the condition of the dispenser 20' when the toilet tank water level 75' has reached its FULL position, the bulk of the air bubble retained within air trap 81' during the charging operation has rotated about edge 59' of partition segment 58' so as to substantially fill horizontal passageway 87' as well as the uppermost portions of vertical passageways 86' and 88', thereby isolating the product solution 103' contained within the inlet/discharge conduit 80' from the toilet tank water 63' contained within passageway 86' of syphon tube 44'. This feature is more clearly illustrated in FIG. 40 which is an enlarged fragmentary view of the air trap portion of the dispenser 20' illustrated in FIG. 39. It is thus clear that the product solution 103' contained within passageway 71', product chamber 69', primary reservoir 65' and inlet/discharge conduit 80' is completely isolated from toilet tank water 63' by means of the air-lock provided in the uppermost sections of passageways 71' and 72' and the air-lock provided in the uppermost sections of passageways 86', 88' and horizontal passageway 87'. As will be appreciated by those skilled in the art, the toilet tank water brought into contact with solid product 21' during the charging cycle will continue to dissolve the solid product until such time as the product solution 103' becomes saturated or until such time as the toilet is flushed and a predetermined quantity or dose-volume of the solution is dispensed. As will also be appreciated by those skilled in the art, the exterior surfaces of solid product 21' are preferably so configured as to permit a uniform degree of surface exposure to the solution 103' along the entire length and width of the solid product. To this end, the exterior surfaces of the solid product may be longitudinally grooved, etc. Uniform surface exposure of the solid product 21' to the solution 103' promotes more uniform erosion of the solid product, and thereby more uniform settling of the solid product into secondary solution reservoir 68'.

FIG. 41 represents the condition of the dispenser when the toilet is flushed and the tank water level drops, thereby exposing air vent 83' and forming a partial vacuum in the syphon tube 44'. Product solution 103' is drawn from the primary reservoir 65' into syphon tube 44'. Transfer of solution 103' from the primary reservoir 65' continues until such time as the solution level reaches edge 67' of partition segment 96', FIG. 42, thereby venting syphon tube 44' and releasing the product solution retained therein into the toilet tank water.

As is also apparent from FIG. 42, uppermost edge 61' of partition segment 33' retains a portion of the concentrated product solution 103' within secondary reservoir 68' after the dispensing cycle has been completed. The solution thus retained will be available to cover rapid multiple flushes of the toilet. In addition, the secondary reservoir 68' serves to prevent the collection of a thick concentrate of solution 103' in the lowermost portions of primary solution reservoir 65'. When the level 75' of the toilet tank water 63' returns to the FULL position illustrated in FIG. 39, the dispenser 20' will likewise be restored to the condition illustrated in FIG. 39, and will remain in that condition during the ensuing quiescent period awaiting the next flush cycle of the toilet.

The dispenser embodiment 20' illustrated in FIG. 35 will discharge a predetermined quantity or dose-volume of product solution 103' from the dispenser each time the toilet is flushed. The dose-volume of solution is substantially equal to the quantity of solution contained within dispenser 20' between lowermost edge 62' of level control partition 32' and lowermost edge 67' of partition segment 96' in addition to the column of product solution contained within passageway 71', but exclusive of the quantity of solution retained within secondary solution reservoir 68'. The quantity of product solution 103' retained in secondary reservoir 68' in turn determined by the vertical location of edge 61' of partition segment 33'. The amount of product solution 103' dispensed during each flush cycle is more easily understood by comparing FIG. 39 which illustrates the condition of the dispenser 20' when the toilet tank water level 75' is FULL and air vent 83' has been blocked by the water with FIG. 42 which illustrates the condition of the dispenser when the solution level within primary solution reservoir 65' has reached lowermost edge 67' of partition segment 96' and the dose-volume of solution within syphon tube 44' has been released.

As has been pointed out earlier herein, the solid, water soluble product 21' contained in product chamber 69' will dissolve in the water introduced during each flush cycle to form product solution 103' until such time as the solution becomes saturated or the toilet is again flushed. As the lower portions of the solid product 21' are consumed by exposure to the liquid, the solid product will settle due to gravity into the secondary reservoir 68' contained within product chamber 69'. Because the volume and exposed surface area of solid product 21' below edge 62' of level control partition 32' remain essentially constant throughout the life of the solid product, the strength or concentration of the solution 103' remains essentially constant throughout the life of the dispenser 20', assuming an adequately long quiescent period for the solution to become saturated is provided intermediate flush cycles. This condition will prevail at least until such time as the overall height of the solid product 21' becomes less than the vertical distance between lowermost edge 62' of level control partition 32' and bottom wall segment 29' of the dispenser.

While the dispenser embodiment illustrated in FIG. 35 incorporates a preferred air trap 81' disposed adjacent the inlet/discharge conduit 80', the air trap utilized to retain an air bubble during the water charging operation may take many different forms. For example, a sudden expansion in cross-section flow area could be provided in vertical inlet passageway 88' followed immediately by a sudden contraction in flow area such that fluid entering the primary reservoir 65' through the inlet/discharge conduit 80' is unable to exert sufficient force on the air bubble trapped within the expanded flow area to expel it through the primary reservoir 65' and out, the air vent 83'. Alternatively, the air trap could take the form of a partial obstruction in inlet/discharge conduit 80', which partial obstruction prevents fluid passing through the conduit from exerting sufficient force on the air bubble retained within the trap from being expelled through the primary reservoir 65' and out the air vent 83'. It is necessary only that the air trap be of sufficient volume and so located that upon cessation of the flow of water past the air trap the air bubble contained therein will attempt to rise into the uppermost reaches of the chamber connecting the syphon tube and the inlet/discharge conduit so as to completely isolate the toilet tank water 63' in the syphon tube from the product solution 103' contained in the inlet/discharge conduit.

FIG. 43 is a fragmentary sectional view of an alternative embodiment of a dispenser 320 suitable for dispensing a surfactant containing solution in accordance with the present invention shown during the water charging operation as the level 375 of water 363 in the toilet tank is rising. The dispenser 320 is basically similar to the dispenser 20' illustrated in FIG. 35. The illustrated portions of dispenser 320 comprise top wall 328, bottom wall segments 329, 353, 354, and 355, sidewall segments 326, 331, 350 and 351, interior level control partition 332, interior partition 395 forming air trap 381 and interior partition segment 396 which in conjunction with the uppermost portion of wall segment 350 forms inlet/discharge conduit 380. As with the embodiment of FIG.

35, a solid, water soluble product 321 is disposed within product chamber 369 such that its lowermost surface rests within secondary solution reservoir 368 defined by interior partition segment 333 having uppermost edge 361. The lowermost edge of level control partition 332 is designated 362, the uppermost edge of wall segment 331 is designated 393, the lowermost edge of sidewall segment 326 is designated 364, the uppermost edge of sidewall segment 350 is designated 359 and the lowermost edge of partition segment 396 is designated 367. Product chamber 369 and primary solution reservoir 365 are initially vented by means of passageways 371 and 372 and air vent 383 defined by edge 364 of sidewall segment 326, the front and back wall portions (not shown) of dispenser 320 and sidewall segment 331. Syphon tube 344 is defined by sidwall segments 350, 351 and 390 as well as the corresponding front and back wall portions (not shown) of dispenser 320. The inlet/discharge port located at the lowermost end of syphon tube 344 is designated 378. As with the embodiment illustrated in FIG. 35, the uppermost portions of the syphon tube are convergent, i.e., the radial distance from uppermost edge 359 of sidewall segment 350 to sidewall segment 390 and to interior partition 395 continually decreases in the direction of liquid flow, at least until the point of vertical alignment with sidewall segment 350. The air trap 381 formed by interior partition 395 is located adjacent the entrance to inlet/discharge conduit 380.

In the condition illustrated in FIG. 43, the toilet tank water 363 has risen sufficiently in syphon tube 344 to trap an air bubble within air trap 381 as it proceeds to fill primary solution reservoir 365 and the lowermost portions of produce chamber 369. As long as the water continues to flow within the syphon tube and inlet/discharge conduit, the trapped air bubble will remain within the confines of the air trap 381. When, however, air vent 383 is blocked by the rising toilet tank water 363 as shown in FIG. 44, fluid flow in the inlet/discharge conduit 380 ceases, and the trapped air bubble rises, thereby providing air-lock isolation of the product solution 303 and the toilet tank water 363 on opposite sides of edge 359 of sidewall segment 350. The product solution 303 at level 302 within passageway 371 is likewise isolated from the toilet tank water by means of the air-lock contained in the uppermost reaches of passageways 371 and 372. The level 301 of product solution 303 within dispenser 320 is defined by lowermost edge 362 of level control partition 332 in a manner similar to that described in connection with embodiment 20' of FIG. 35. When the toilet is flushed, dispenser embodiment 320 reacts in a manner similar to embodiment 20' described in connection with FIG. 35. When the level of solution in primary reservoir 365 reaches lowermost edges 367 of partition segment 396, the column of liquid retained within syphon tube 344 is vented, thereby dispensing a predetermined quantity of product solution 303 into the toilet tank through inlet/discharge port 378.

While the exemplary embodiments of dispensers 20' and 320 may be constructed by adhesively securing sections of relatively rigid Plexiglass (Registered Trademark of Rohm & Haas Company) to one another, other relatively rigid materials which are substantially inert with respect to the intended product and aqueous solutions thereof can be used to construct the dispensers. Furthermore, the dispensers may be constructed or formed at high speed and relatively low cost utilizing various manufacturing techniques well known in the art. For example, the dispensers could be vacuum thermoformed in two sections of a material such as polyvinyl chloride having an initial thickness of about 0.020 inches, the solid, water soluble product inserted therebetween and the two sections thereafter secured to one another as by heat sealing, adhesives, etc. along a line of contact substantially coinciding with the location of section line 36—36 of FIG. 35.

In a particularly preferred embodiment of the present invention, a passive dosing dispenser of the type generally illustrated in FIG. 1 or FIG. 12 is utilized to dispense a predetermined quantity of disinfectant containing solution, while a passive dosing dispenser as generally illustrated in FIG. 26 or as generally illustrated in FIG. 35 or FIG. 43 is utilized to simultaneously dispense a predetermined quantity of surfactant containing solution. While such dispensing embodiments may, if desired, be integrally combined with one another as generally indicated in FIGS. 10 and 11, in a preferred embodiment the front and back sections for a dual dispensing apparatus are vacuum thermoformed from sheets of material such as 0.015 inch thick polyvinyl chloride, the disinfectant containing cake and the surfactant containing cake are inserted intermediate the two vacuum thermoformed sections as generally outlined in the aforementioned patent applications of Robert S. Dirksing, and the two sections are thereafter secured to one another as by heat sealing, adhesives, etc. to form an integral dual dispenser. In a particularly preferred embodiment, the dual dispenser is so configured that the surfactant containing cake is located vertically overhead the disinfectant containing cake. The integral dual dispenser unit is preferably equipped with adjustable hanger means for properly positioning the apparatus relative to the FULL level of the water contained in the toilet tank. If desired, closure means in the form of a suitable cover, pressure sensitive adhesive tapes, or the like may also be provided with the dual dispenser to seal the entry and discharge ports of the dispensing apparatus upon disposal to prevent adverse chemical reactions from occurring once the dispensing apparatus has been removed from the toilet tank for disposal.

To demostrate the effectiveness of the cleansing and disinfecting method described herein, an exemplary embodiment of a dual dispensing apparatus was constructed and subjected to testing.

A solid, compacted disinfectant containing cake was prepared by mixing LiOCl (Form 2), as available from Lithium Corporation of America, Bessemer City, North Carolina, with HTH [65% Ca(CoCl)$_2$] NaCl and Na$_2$SO$_4$ in the proportions hereinafter set forth and subjecting the granular mixture to a compaction pressure of about 2.5 tons per square inch on a Stokes Model R Tablet Press:

| Ingredient | Grams |
|---|---|
| LiOCl (Form 2) | 27.2 |
| HTH [65% Ca(OCl)$_2$] | 43.9 |
| NaCl | 21.7 |
| Na$_2$SO$_4$ | 7.2 |
| | 100.0 |

This composition had a LiOCl:Ca(OCl)$_2$ weight ratio of about 0.29:1, and an available chlorine level (AvCl$_2$) of about 38% to 39%. The cake had a specific gravity of about 1.7, and dimensions of about 3.5 inches by about 2 inches by about 0.5 inches.

A solid, compacted surfactant containing cake was prepared by mixing the ingredients hereinafter set forth in a batch amalgamator, followed by milling and then extrusion to form a rectangular slab having dimensions of about 3.625 inches in width by about 2.125 inches in height by about 0.5 inches thick:

| Ingredient | Grams |
| --- | --- |
| Sodium paraffin sulfonate (Hostapur, approximately 84% active, as available from American Hoechst, Somerville, N.J.) | 52.2 |
| Acid Green 2G (as available from Sandoz, Hanover, N.J.) | 3.7 |
| NaBr | 1.9 |
| Perfume | 7.2 |
| | 65.0 |

The surfactant containing cake was thereafter coated with talcum powder to prevent it from sticking to the sides of the dispensing apparatus.

The solid disinfectant containing and surfactant containing cakes were incorporated in a dual compartment dispenser vacuum thermoformed in two segments from 0.015 inch thick polyvinyl chloride. The configuration of the integrally formed dual compartment dispenser was such that the surfactant containing cake was placed vertically overhead the disinfectant containing cake. The portion of the dispensing apparatus housing the surfactant containing cake was of a configuration generally similar to those described in connection with FIGS. 35 and 43, while the portion of the dispensing apparatus housing the disinfectant containing tablet was of a configuration generally similar to that described in connection with FIG. 12. The measuring cavity and inlet conduit of the disinfectant containing portion of the dual dispenser was so sized that approximately 12 cubic centimeters of disinfectant containing solution was dispensed with each flush cycle of the toilet. The surfactant containing portion of the dispenser were so sized that approximately two cubic centimeters of surfactant containing solution was dispensed with each flush cycle of the toilet.

The aforedescribed exemplary embodiment of a dual dispenser for carrying out the cleansing and disinfecting method of the present invention provided an excellent release of both the disinfectant containing solution and the surfactant containing solution throughout the life of the unit. In order to ascertain the effective life of the co-dispensing operation, the reaction of the hypochlorite contained in the disinfectant containing solution with the dye contained in the surfactant containing solution was observed in the toilet bowl. When both chemicals are present in the water at the same time, the color is bleached from the dye, thereby causing the water to change from a blue-green tint to colorless within a few minutes. The presence of this reaction serves as an indicator that both portions of the dispensing apparatus are functioning in the intended manner. Accordingly, when no color is visibly delivered to the toilet bowl, or when the color delivered is not dissipated shortly thereafter, the dispenser is in need of replacement. It should of course be recognized that several flushes of the toilet will normally be required to fill the solution reservoir in the disinfectant containing portion of the dispenser when the dispenser is initially placed in service. During this limited period, the aforementioned hypochlorite-dye reaction will not be present due to the lack of disinfectant containing solution in the water.

While the life of the aforedescribed exemplary dispenser will vary depending upon the water temperature involved due to the effect of temperature on dissolution of this particular surfactant containing cake, it is anticipated that in 70° F. tank water the dual dispenser embodiment described above will provide effective cleansing and disinfecting for approximately 400 flush cycles of a toilet, while in 40° F. tank water approximately 700 flush cycles are anticipated. Depending upon such variables as frequency of flushing, number of occupants in the home, etc., this typically provides a useful life ranging from approximately 2 to approximately 8 weeks in the home environment.

As has been pointed out earlier herein, by appropriate sizing of the surfactant containing and disinfectant containing cakes, dual dispensing apparatus of the present invention can be provided so that both cakes are substantially consumed at about the same point in time, thereby minimizing waste of either component.

While particular embodiments of the present invention have been described, it will be obvious to those skilled in the art that various changes and modifications can be made without departing from the spirit and scope of the invention and it is intended to cover, in the appended claims, all such modifications that are within the scope of this invention.

What is claimed is:

1. A method for cleansing and disinfecting a flushing toilet containing water and comprising a toilet tank and a toilet bowl each time said toilet is flushed, said method comprising:
   (a) forming a quantity of surfactant containing solution by exposing a first solid, water soluble, surfactant containing cake to a first quantity of said water within a first passive dispensing apparatus immersed in said toilet tank;
   (b) isolating said first cake and said surfactant containing solution in said first passive dispensing apparatus from the water surrounding said first dispensing apparatus;
   (c) forming a quantity of disinfectant containing solution by totally immersing a second solid, water soluble disinfectant containing cake in a second quantity of said water within a second passive dispensing apparatus immersed in said toilet tank;
   (d) isolating said second cake and said disinfectant containing solution in said second passive dispensing apparatus from the water surrounding said second dispensing apparatus;
   (e) flushing said toilet, thereby lowering the water level in said toilet tank from a first elevation to a second elevation;
   (f) discharging a predetermined quantity of said surfactant containing solution of substantially constant strength from said first passive dispensing apparatus in response to the water level in said toilet tank being lowered from said first elevation to said second elevation; and
   (g) discharging a predetermined quantity of said disinfectant containing solution substantially free of undissolved solids from said second passive dispensing apparatus in response to the water level in said toilet tank being lowered from said first elevation to said second elevation.

2. The method of claim 1, wherein the discharge of said predetermined quantity of surfactant containing solution from said first passive dispensing apparatus is accomplished utilizing suction created by the lowering of said water level in said toilet tank and the gravitational head of said surfactant containing solution.

3. The method of claim 1, including the step of isolating said solid, water soluble, surfactant containing cake from said surfactant containing solution during quiescent periods intermediate flushes of said toilet.

4. The method of claim 2 or 3 wherein the discharge of said predetermined quantity of disinfectant containing solution from said second passive dispensing apparatus is accomplished utilizing suction created by the lowering of said water level in said toilet tank, said suction being sufficient to overcome the gravitational head of said disinfection containing solution.

5. A cleansing and disinfecting apparatus for cleansing and disinfecting a flushing toilet containing water and comprising a toilet tank and a toilet bowl each time said toilet is flushed, said apparatus comprising:
(a) a first passive dispensing apparatus for immersion in the water in said toilet tank, said first dispensing apparatus containing a first solid, water soluble, surfactant containing cake for exposure to a first quantity of said water to form an aqueous surfactant containing solution, said first dispensing apparatus including means for isolating said first cake and said surfactant containing solution from the water surrounding said first dispensing apparatus and means for discharging a predetermined quantity of said surfactant containing solution of substantially constant strength into said toilet tank in response to the water level in said toilet tank being lowered from a first elevation to a second elevation when said toilet is flushed; and
(b) a second passive dispensing apparatus for immersion in the water in said toilet tank secured to said first passive dispensing apparatus, said second dispensing apparatus containing a second solid, water soluble, disinfectant containing cake for exposure to a second quantity of said water to form an aqueous disinfectant containing solution, said second dispensing apparatus including means for isolating said second cake and said disinfectant containing solution from the water surrounding said second dispensing apparatus and means for discharging a predetermined quantity of said disinfectant containing solution substantially free of undissolved solids into said toilet tank in response to the water level in said toilet tank being lowered from a first elevation to a second elevation when said toilet is flushed.

6. The cleansing and disinfectant apparatus of claim 5, wherein said first passive dispensing apparatus includes means for isolating said first solid, water soluble surfactant containing cake from said surfactant containing solution during quiescent periods intermediate flushes of said toilet.

7. The cleansing and disinfectant apparatus of claim 5, wherein the point at which said predetermined quantity of surfactant containing sulution is withdrawn from said first passive dispensing apparatus is at a lower elevation than the maximum level achieved by said solution in said dispensing apparatus during quiescent periods intermediate flushes of said toilet, thereby providing a gravitational head to assist in discharging said surfactant containing solution from said dispensing apparatus.

8. The cleansing and disinfecting apparatus of claim 6 or 7, wherein said second passive dispensing apparatus includes a solution reservoir for totally immersing said second solid, water soluble disinfectant cake in said second quantity of water such that the surface of said disinfectant containing solution is at a first elevation higher than the top of said cake during quiescent periods intermediate flushes of said toilet, said second passive dispenser further comprising means for raising said predetermined quantity of disinfectant containing solution to a second elevation higher than said first elevation in discharging said disinfectant containing solution from said second dispensing apparatus.

9. The cleansing and disinfecting apparatus of claim 8, wherein said first passive dispensing apparatus and said second dispensing apparatus comprise an integral structure.

10. The cleansing and disinfecting apparatus of claim 9, wherein said first passive dispensing apparatus is positioned in said toilet tank at a higher elevation than said second passive dispensing apparatus.

11. The cleansing and disinfecting apparatus of claim 8, including common suspensory means for immersing said first passive dispensing apparatus and said second passive dispensing apparatus in the water contained in said toilet tank.

12. The cleansing and disinfecting apparatus of claim 11, including means for simultaneously vertically adjusting the position of said first passive dispensing apparatus and said second passive dispensing apparatus in said toilet tank.

* * * * *

UNITED STATES PATENT AND TRADEMARK OFFICE
CERTIFICATE OF CORRECTION

PATENT NO.   : 4,216,027
DATED        : August 5, 1980
INVENTOR(S)  : Dwight E. Wages It is certified that error appears in the above-identified patent and that said Letters Patent are hereby corrected as shown below:

Title Page, Column 2, line 19, after "tank", insert -- in response to the water level in the tank being lowered from a first elevation to a second elevation --.

Column 5, line 67, "Nchloroi-" should read -- N-chloroi- --.
Column 9, line 31, "Litium" should read -- Lithium --.
Column 10, line 47, after "abandoned" insert -- , --.
Column 19, line 37, "wal" should read -- wall --.
Column 19, line 56, "Plexiglass" should read -- Plexiglas --.
Column 21, line 17, "perios" should read -- periods --.
Column 22, line 14, "whle" should read -- while --.
Column 25, line 37, "83+" should read -- 83' --.
Column 25, line 41, "26" should read -- 36 --.
Column 25, line 49, "transfer" should read -- thereafter --.
Column 25, line 56, "inlet/ discharge" should read -- inlet/discharge --.
Column 26, line 19, "28" should read -- 38 --.
Column 27, line 62, after "68'" insert -- is --.
Column 29, line 16, "sidwal" should read -- sidewall --.
Column 29, line 34, "produce" should read -- product --.

UNITED STATES PATENT AND TRADEMARK OFFICE
CERTIFICATE OF CORRECTION

PATENT NO. : 4,216,027

DATED : August 5, 1980

INVENTOR(S) : Dwight E. Wages

It is certified that error appears in the above-identified patent and that said Letters Patent are hereby corrected as shown below:

Column 29, line 62, "Plexiglass" should read -- Plexiglas --.

Column 30, line 45, "demostrate" should read -- demonstrate --.

Column 34, line 5, "disinfectant" should read -- disinfecting --

Column 34, line 24, "surfact" should read -- surface --.

Signed and Sealed this

Thirtieth Day of December 1980

[SEAL]

Attest:

SIDNEY A. DIAMOND

Attesting Officer

Commissioner of Patents and Trademarks